United States Patent [19]

Kanda et al.

[11] Patent Number: 5,008,271
[45] Date of Patent: Apr. 16, 1991

[54] DC-88A DERIVATIVES

[75] Inventors: Yutaka Kanda, Houston, Tex.; Tohru Yasuzawa, Sakai, Japan; Hiromitsu Saito, Sagamihara, Japan; Hiroshi Sano, Machida, Japan; Eiji Kobayashi; Makoto Morimoto, both of Shizuoka, Japan

[73] Assignee: Kyowa Hakko Kogyo Co., Ltd., Tokyo, Japan

[21] Appl. No.: 423,788

[22] Filed: Oct. 18, 1989

[30] Foreign Application Priority Data

Oct. 21, 1988 [JP] Japan .................................. 63-265582
Mar. 15, 1989 [JP] Japan .................................. 64-62572

[51] Int. Cl.$^5$ ..................... A61K 31/44; A61K 31/40; C07D 471/12; C07D 209/02
[52] U.S. Cl. .................................. 514/292; 514/414; 546/84; 548/455
[58] Field of Search ..................... 546/84, 14; 548/455; 514/292, 414

[56]  References Cited

U.S. PATENT DOCUMENTS

| | | | |
|---|---|---|---|
| 4,169,888 | 10/1979 | Hanka et al. ........................... | 546/84 |
| 4,400,518 | 8/1983 | Wierenga ............................ | 548/455 |
| 4,413,132 | 11/1983 | Wierenga ............................ | 548/455 |
| 4,423,228 | 12/1983 | Wierenga ............................ | 548/455 |
| 4,423,229 | 12/1983 | Wierenga ............................ | 548/455 |
| 4,423,230 | 12/1983 | Wierenga ............................ | 548/455 |

FOREIGN PATENT DOCUMENTS

| | | | |
|---|---|---|---|
| 0154445 | 2/1985 | European Pat. Off. ............ | 548/455 |
| 0271581 | 6/1988 | European Pat. Off. ............ | 548/455 |
| 0318056 | 11/1988 | European Pat. Off. ............ | 548/455 |
| 0339681 | 11/1989 | European Pat. Off. ............ | 548/455 |
| WO87/06265 | 10/1987 | PCT Int'l Appl. ................. | 548/455 |
| WO88/04659 | 6/1988 | PCT Int'l Appl. ................. | 548/455 |

OTHER PUBLICATIONS

Warpehoski et al., J. Med. Chem., vol. 31 (1988), pp. 590–603.
Wierenga et al., Adv. Enzyme Regul., Antitumor Analogs of CC-1065, pp. 143–155.

Primary Examiner—Mary C. Lee
Assistant Examiner—Joseph K. McKane
Attorney, Agent, or Firm—Fitzpatrick, Cella, Harper & Scinto

[57]  ABSTRACT

A novel DC-88A derivative represented by general formula:

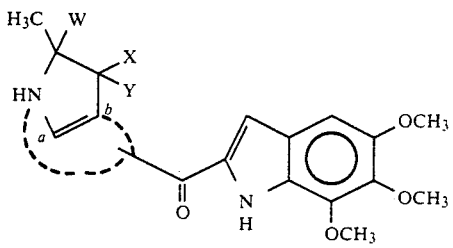

wherein

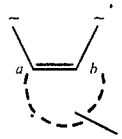

represents

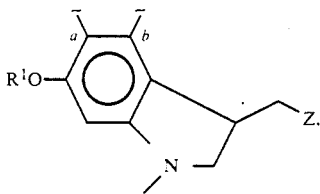

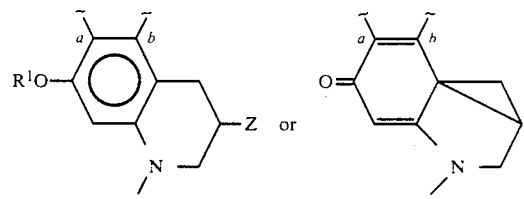

has an excellent antitumor activity and is useful as an antitumor agent.

15 Claims, No Drawings

DC-88A DERIVATIVES

BACKGROUND OF THE INVENTION

The present invention relates to novel DC-88A derivatives. The derivatives have an excellent antitumor activity and are useful as antitumor agents.

WO 87/06265 (EP-A-0271581) discloses DC-88A produced by microorganisms belonging to the genus Streptomyces exhibits not only an antibacterial activity against various bacteria but also an antitumor activity against lymphocytic leukemia P388, etc.

DC-88A has the following structure.

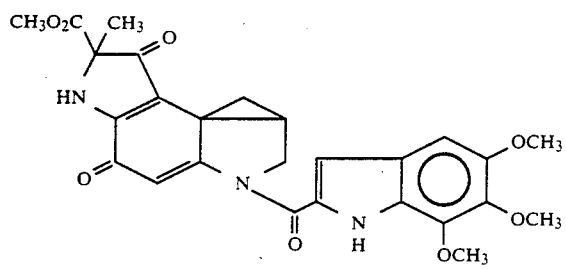

DC-89A1 which is a compound having a structure similar to DC-88A is disclosed in WO87/06265; DC-89A2, DC-89B1 and DC-89B2 are described in Japanese Patent Application No. 182866/88.

DC-89A1, DC-89A2, DC-89B1 and DC-89B2 have the following structures.

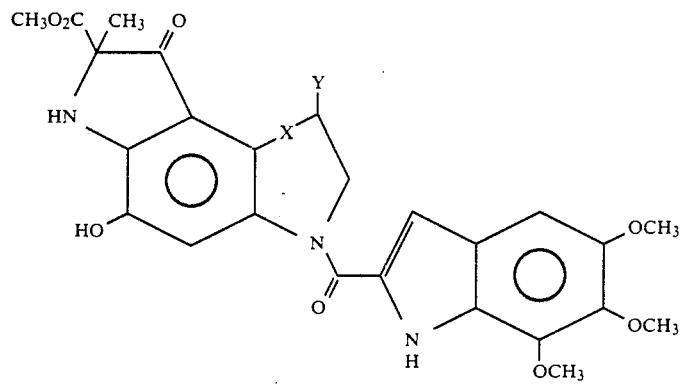

DC-89A1: X=—CH$_2$—, Y=Cl
DC-89A2: X=single bond, Y=—CH$_2$Cl
DC-89B1: X=—CH$_2$—, Y=Br
DC-89B2: X=single bond, Y=—CH$_2$Br These compounds show an antibacterial activity against various bacteria and an antitumor activity against lymphocytic leukemia P388, etc.

Further, in commonly owned U.S. patent application filed on Aug. 11, 1989, which corresponds to European Patent Application No. 89 114 896.7, DC-88A derivatives are described.

CC-1065 and its derivatives which are structurally similar to DC-88A and exhibit an antitumor activity are also disclosed in U.S. Pat. No. 4,169,888; Japanese Published Unexamined Patent Application No. 64695/79; EP-A-0154445, Japanese Published Unexamined Patent Application No. 193989/85; and WO 88/04659.

SUMMARY OF THE INVENTION

The object of the present invention is to provide a DC-88A derivative having superior properties over DC-88A, DC-89A1, DC-89A2, DC-89B1 and DC-89B2.

In accordance with the present invention, there is provided novel DC-88A derivatives represented by general formula (A):

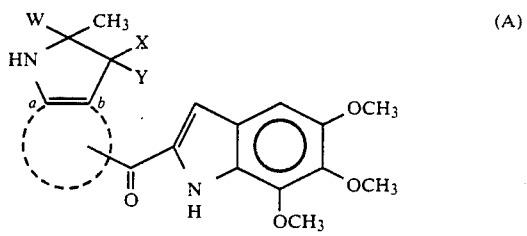

wherein one of X and Y is hydrogen, and the other is —OR$^2$ wherein R$^2$ represents hydrogen, —CH , —COCH or —COPh wherein Ph represents unsubstituted or substituted phenyl,
or X and Y are combined together to form=O;

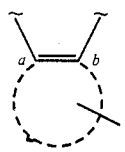

represents (I)

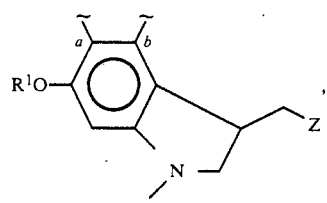

,

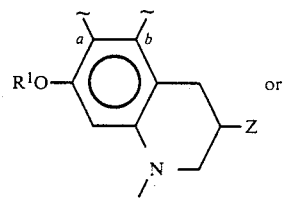

or

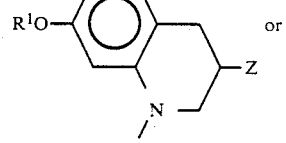

(II)

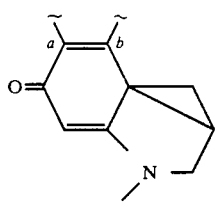

wherein Z represents chlorine or bromine; $R^1$ represents hydrogen, straight or branched alkyl having 1 to 4 carbon atoms, $-COR^3$, $-CONR^4R^5$, $-CO_2R^6$, $-SiR^7R^8R^9$ or $-CH_2OCH_3$ wherein $R^3$ represents straight or branched alkyl having 1 to 14 carbon atoms, or unsubstituted or substituted phenyl, each of $R^4$ and $R^5$ independently represent straight or branched alkyl having 1 to 4 carbon atoms, $R^6$ represents straight or branched alkyl having 1 to 4 carbon atoms, allyl or aralkyl, each of $R^7$, $R^8$ and $R^9$ independently represents straight or branched alkyl having 1 to 4 carbon atoms; W represents hydrogen, allyl, $-CO_2R^{10}$, $-COR^4$ or $-CH_2OR^2$ wherein $R^{10}$ represents straight or branched alkyl having 1 to 5 carbon atoms, substituted alkyl having 1 to 5 carbon atoms, allyl or benzyl, $R^4$ and $R^2$ have the same significances as defined above; provided that when

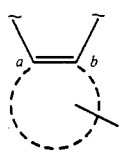

represents

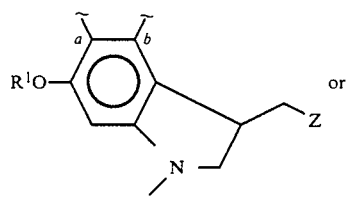

or

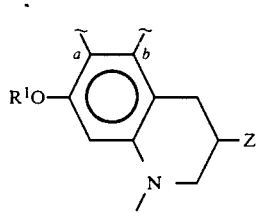

where $R^1$ is hydrogen, and W is $-CO_2CH_3$; or when (III)

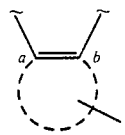

represents

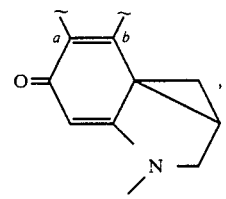

and W is $-CO_2CH_3$; one of X and Y represents hydrogen, and the other represents $-OR^2$ wherein $R^2$ has the same significance as defined above.

DETAILED DESCRIPTION OF THE INVENTION

Hereinafter, compounds represented by the general formula (A) having formulae (I), (II) and (III) are referred to as Compounds (I), (II) and (III), respectively.

In the definition for $R^2$ and $R^3$ in general formula (A), the substituted phenyl means substituted phenyl with 1 to 3 substituents which may be the same or different. The substituents include, for example, chlorine, bromine, iodine, nitro, amino, hydroxy, lower alkoxy in which the alkyl moiety means straight or branched alkyl having 1 to 4 carbon atoms such as methyl, ethyl, propyl, isopropyl, butyl, isobutyl, sec-butyl, tert-butyl, etc.

In the definition for $R^1$, $R^4$, $R^5$, $R^6$, $R^7$, $R^8$ and $R^9$, as the straight or branched alkyl having 1 to 4 carbon atoms, mention may be made of the same groups as defined in the alkyl moiety of the lower alkoxy for the substituents of the substituted phenyl in the definition for $R^2$ and $R^3$. In the definition for $R^{10}$ as the straight or branched alkyl having 1 to 5 carbon atoms, pentyl, neopentyl, etc. in addition to the same groups as defined for $R^1$, $R^4$, $R^5$, $R^6$, $R^7$, $R^8$ and $R^9$ are mentioned. In the definition for $R^3$, the straight or branched alkyl having 1 to 14 carbon atoms includes, for example, hexyl, heptyl, octyl, nonyl, decyl, undecyl, dodecyl, tridecyl and tetradecyl in addition to the same groups as defined for $R^{10}$.

In the definition for $R^6$, the aralkyl means aralkyl having 7 to 13 carbon atoms, such as benzyl, phenethyl, phenylpropyl, benzhydryl, etc.

The substituents for the substituted alkyl in $R^{10}$ may be same or different, and include, for example, hydroxy, amino and carboxy. One to 3 arbitrary hydrogen atoms in the alkyl are substituted therewith.

Next, processes for producing Compounds (I), (II) and (III) ar described below.

(Step 1)

Compound (I-1), which is Compound (I) wherein W is $CO_2R^{10}$, X and Y are combined together to form=O and $R^1$ represents the other groups than hydrogen,can be prepared by the following step.

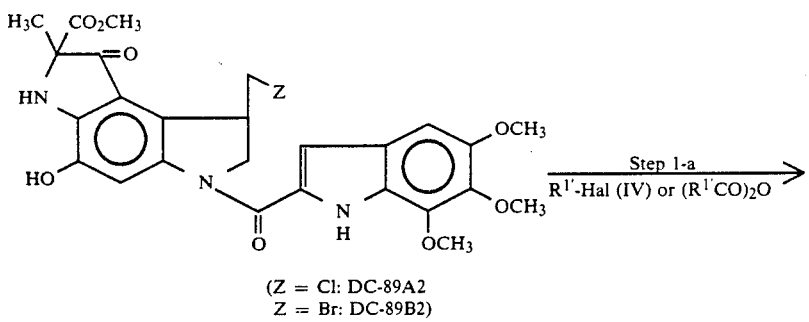

(Z = Cl: DC-89A2
Z = Br: DC-89B2)

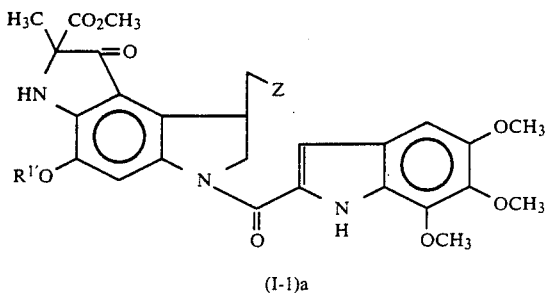

(I-1)a

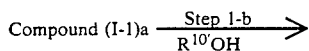

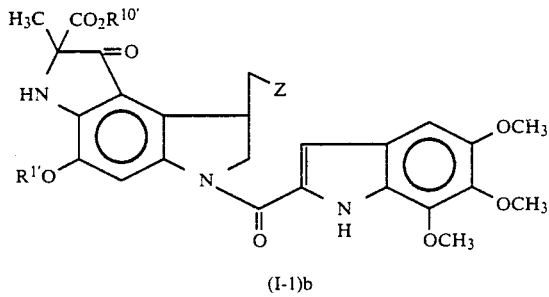

(I-1)b

Compound (I-1)a, which is Compound (I-1) wherein $R^{10}$ is methyl, can be prepared by reacting DC-89A2 or DC89B2 obtained by culturing a microorganism belonging to the genus Streptomyces with Compound (IV) represented by formula:

$$R^{1'}-Hal \qquad (IV)$$

wherein ¹represents the other groups than hydrogen in the definition of $R^1$ and Hal represents chlorine, bromine or iodine, in an inert solvent in the presence of a base (Step 1-a). Furthermore, Compound (I-1)a may also be prepared by using carboxylic acid anhydride in stead of Compound (IV).

As the base, mention may be made of potassium carbonate, potassium t-butoxide, sodium hydride, triethylamine, dimethylaminopyridine, pyridine, imidazole, etc. As the inert solvent, dimethylformamide (hereinafter referred to as DMF), tetrahydrofuran (hereinafter referred to as THF), methylene chloride, acetonitrile, toluene, benzene, pyridine etc. are used singly or as admixture. Compound (IV) or carboxylic acid anhydride is used in 1 to 2 molar equivalents based on DC-89A2 or DC-89B2. The base is also used in 1 to 2 molar equivalents based on DC-89A2 or DC-89B2. The reaction is carried out generally at $-30$ to $50°$ C. and completed in 2 hours to one day.

Compound (I-1)b, which is Compound (I-1) wherein $R^{10}$ represents the other groups than methyl, can be obtained by reacting Compound (I-1)a with $R^{10'}OH$ wherein $R^{10'}$ is the other groups than xethyl in the definition of $R^{10}$ in an inert solvent or in the absence of any solvent in the presence of a base (Step 1-b). As the inert solvent, methylene chloride, chloroform, THF, toluene, etc. are used singly or as admixture. As the base, potassium carbonate, sodium carbonate, sodium hydrogencarbonate, triethylamine, etc. may be used generally in 0.1 to 2 molar equivalents based on Compound (I-1)a. $R^{10'}OH$ is used in 2 molar equivalents to in a largely excessive amounts when the $R^{10'}OH$ functions as a solvent, based on Compound (I-1)a. The reaction is generally carried out at $-20°$ to $40°$ C. and completed in one hour to 3 days.

(Step 2)

Compound (I-2)a, which is Compound (I) wherein W is $CO_2CH_3$, and one of X and Y represents hydrogen and the other represents OH, can be prepared by the following step (Step 2-a)

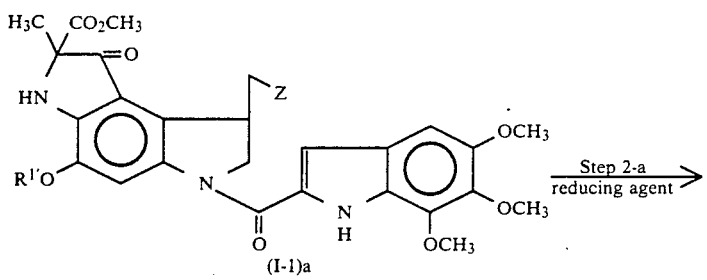

(I-1)a

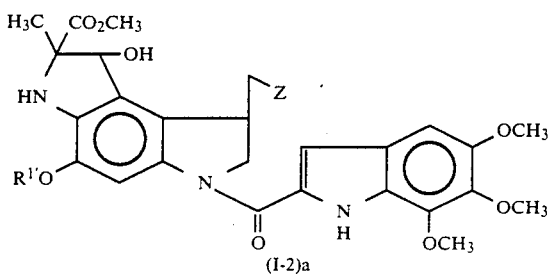

(I-2)a

The reducing agent includes, for example, NaBH$_4$, NaBH$_3$CN, NaAλ(OCH$_2$CO$_2$OCH$_3$)$_2$H$_2$, etc. The reducing agent is generally used in 1 to 3 molar equivalents based on Compound (I-1)a. As the inert solvent, water, methanol, ethanol, t-butanol, THF, diethyl ether, toluene, etc. are used singly or as admixture. The reaction is generally carried out at −50° to 80° C. and completed in one hour to one day.

Compound (I-2)b, which is Compound (I) wherein W is CH$_2$OH, and one of X and Y represents hydrogen and the other represents OH, can be prepared in a manner similar to Step 2-a except for using as a reducing agent, LiB[CH(CH$_3$)C$_2$H$_5$]$_3$H, LiB(C$_2$H$_5$)$_3$H, LiAλH$_4$, etc. (Step 2-b).

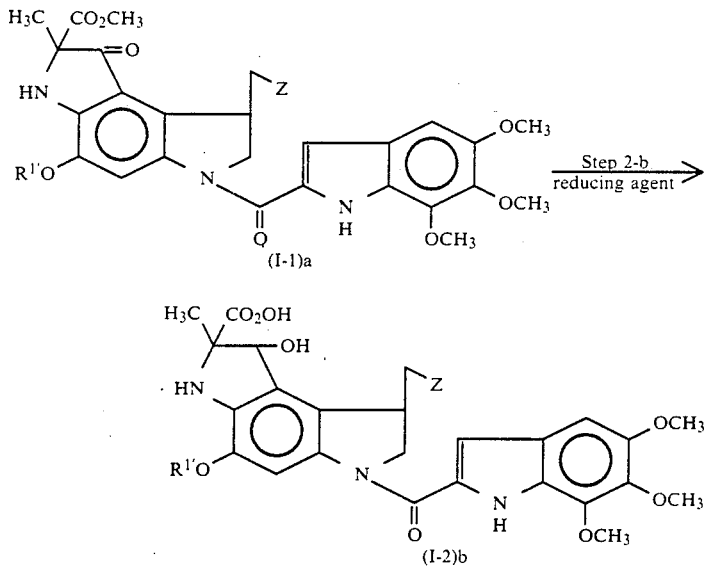

(I-1)a (I-2)b (Step 3)

Compound (I-3), which is Compound (I) wherein W is CO$_2$CH$_3$, and one of X and Y represents hydrogen and the other represents OR$^{2'}$ wherein R$^{2'}$ represents the other groups than hydrogen in the definition of R$^2$, can be prepared by reacting Compound (I-2)a with an acylating agent such as acetyl chloride, acetic anhydride, benzoyl chloride, etc. in an inert solvent in the presence of a base.

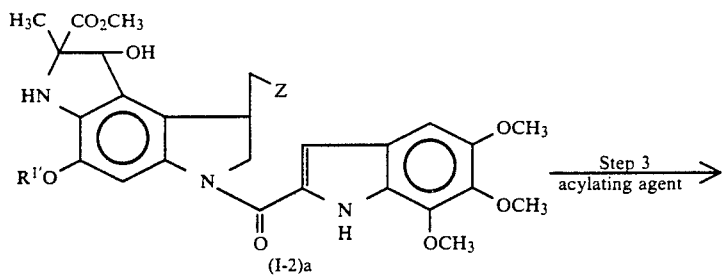

(I-2)a

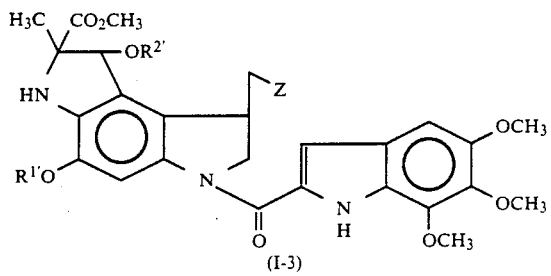

(I-3)

As the inert solvent, methylene chloride, THF, DMF, acetonitrile, pyridine, toluene, etc. are used singly or as admixture. As the base, triethylamine, pyridine, dimethylaminopyridine, etc. are generally used in 0.1 to 2 molar equivalents based on Compound (I-2)a. However, when the base also functions as a solvent, the amount of the base is not limited thereto. The acylating agent is used in 1 to 100 molar equivalents based on Compound (I-2)a. The reaction is generally carried out at −20 to 80° C. an completed in an hour to one day.

(Step 4)

Compound (I-4), which is Compound (I) wherein W is CH₂OCOCH₃, and one of X and Y represents hydrogen and the other represents OH,can be prepared by reacting Compound (I-2)b with an acylating agent such as acetyl chloride, acetic anhydride, etc. in an inert solvent in the presence of a base.

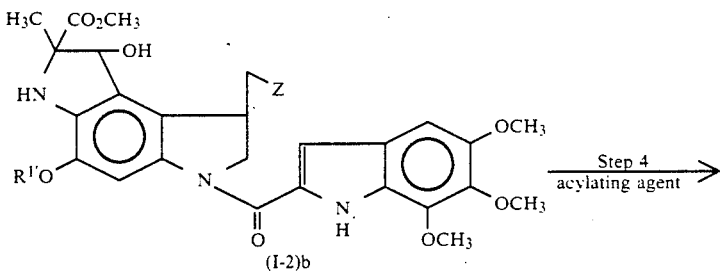

(I-2)b

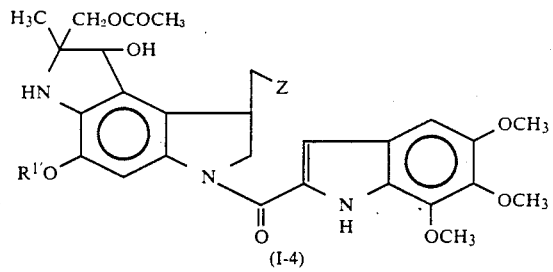

(I-4)

As the inert solvent, methylene chloride, THF, DMF, acetonitrile, pyridine, toluene, etc. are used singly or as admixture. As the base, triethylamine, pyridine, dimethylaminopyridine, etc. are generally used in 0.1 to 2 molar equivalents based on Compound (I-2)b. However, when the base also functions as a solvent, the amount is not limited thereto. The acylating agent is used in 1 to 100 molar equivalents based on Compound (I-2)b. The reaction is generally carried out at −20 to 80° C. and completed in an hour to one day.

Compound (I-5), which is Compound (I) wherein W is hydrogen, and one of X and Y represents hydrogen and the other represents OH,can be prepared by reacting Compound (I-1)a with a reducing agent in an inert solvent.

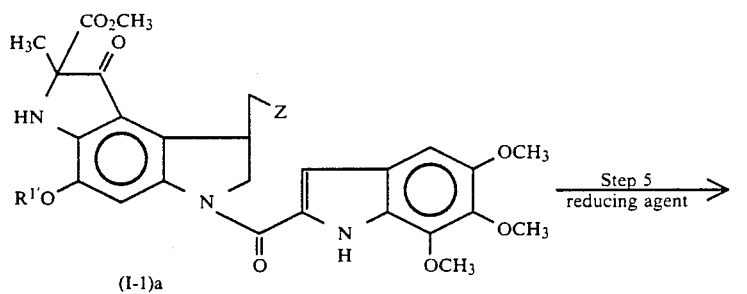

(I-1)a

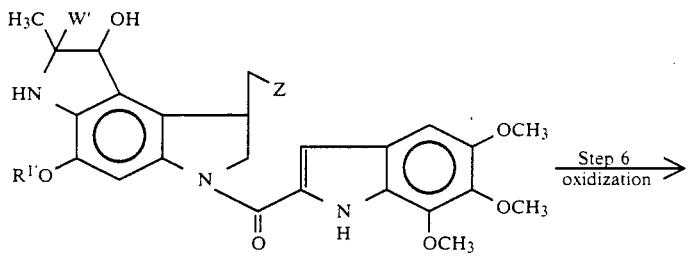

(I-5)

The reducing agent includes, for example, NaBH$_4$, NaBH$_3$CN, LiB[CH(CH$_3$)C$_2$H$_5$]$_3$H, LiB(C$_2$H$_5$)$_3$H, etc. The reducing agent is generally used in 1 to 10 molar equivalents based on Compound (I-1)a. As an inert solvent, water, methanol, ethanol, t-butanol, THF, diethyl ether, toluene, etc. are used singly or as admixture. The reaction is generally carried out at $-50$ to $80°$ C. and completed in an hour to one day.

(Step 6)

Compound (I-6), which is Compound (I) wherein W is hydrogen or CH$_2$OR$^{2'}$ wherein R$^{2'}$ is hydrogen or COCH$_3$, and X and Y are combined together to form =O, can be prepared by oxidizing Compound (I-2)b, (I-4) or (I-5) in an inert solvent. As the inert solvent, diethyl ether, THF, etc. are used. As the oxidizing agent, manganese dioxide, etc. are generally used in 0.5 to 3-fold amounts in a weight ratio based on Compound (I-2)b, (I-4) or (I-5). The reaction is generally carried out at $-20$ to $50°$ C. and completed in 5 hours to 2 days.

(I-2)b W' = CH$_2$OH
(I-4) W' = CH$_2$OCOCH$_3$
(I-5) W' = H

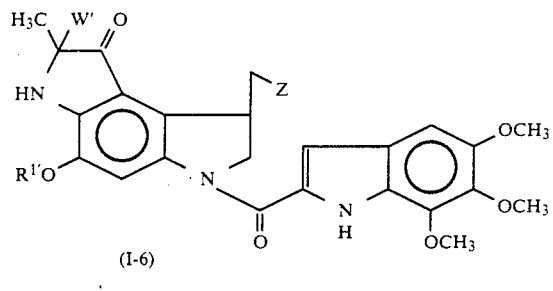

(I-6)

(Step 7)

Compound (I-7), which is Compound (I) wherein W is allyl, and X and Y are combined together to form =O, can be prepared by reacting Compound (I-1)c, which is Compound (I-1)b wherein R$^{10'}$ is allyl, with tetrakis-triphenylphosphine palladium in an inert solvent in the presence of triphenylphosphine. As the inert solvent, methylene chloride, chloroform, THF, etc. may be used. Triphenylphosphine and tetrakis-triphenylphosphine palladium are used in 0.05 to 1 molar equivalent based on Compound (I-1)c. The reaction is generally carried out at $-20$ to $30°$ C. and completed in 20 minutes to 5 hours.

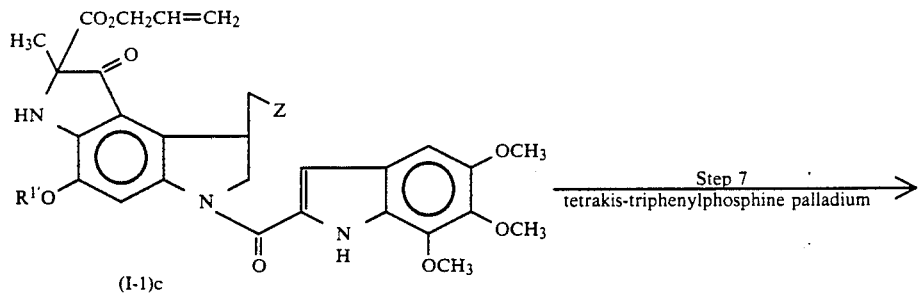

(Step 8)

(Step 7) tetrakis-triphenylphosphine palladium tion is generally carried out at −78 to −30° C. and completed in 30 minutes to 3 hours.

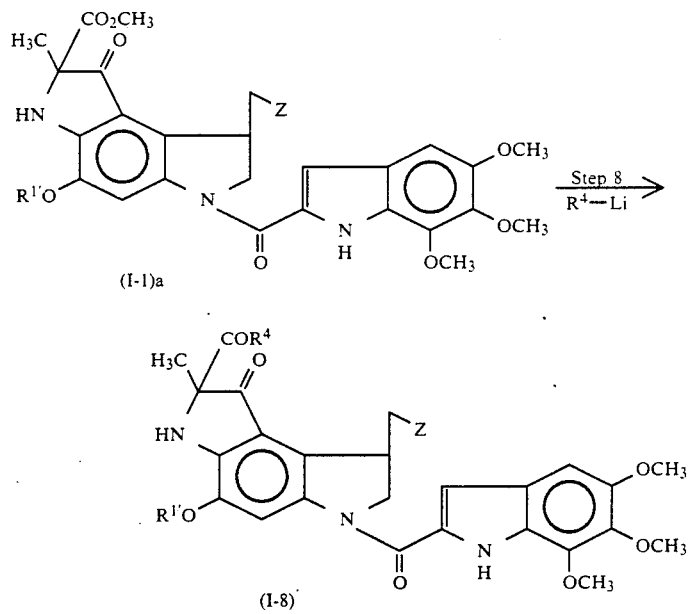

Compound (I-8), which is Compound (I) wherein W is COR$^4$, and X and Y are combined together to form-=O, can be prepared by reacting Compound (I-l)a with R$^4$-Li in an inert solvent. As the inert solvent, THF, diethyl ether, etc. may be used. R$^4$-Li is used in 1 to 2 molar equivalents based on Compound (I-1)a. The reac- (Step 9)

Compound (I-9), which is Compound (I) wherein R$^1$ is hydrogen, can be prepared by using Compound (I-1)b, (I-2)a, (I-2)b, (I-3), (I-4), (I-5), (I-6), (I-7) or (I-8) wherein R$^{1''}$ is either −SiR$^7$R$^8$R$^9$ or −CH$_2$OCH$_3$ as the starting compound.

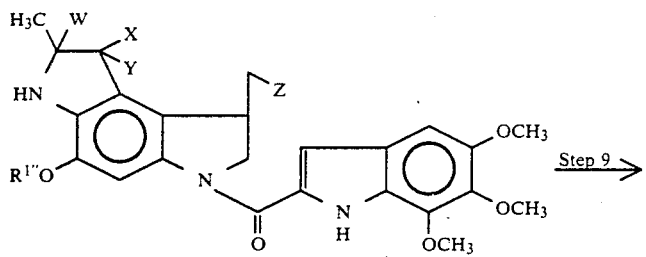

(I-1)b, (I-2)a, (I-2)b, (I-3),
(I-4), (I-5), (I-6), (I-7), (I-8)

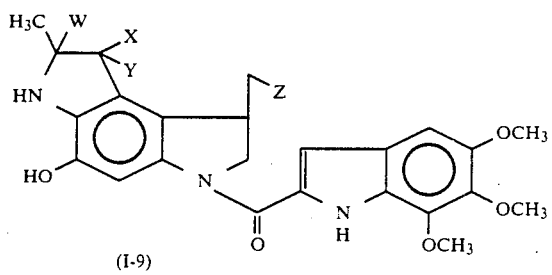

(I-9)

Compound (I-9) can be prepared by reacting Compound (I-1)b, (I-2)a, (I-2)b, (I-3), (I-4), (I-5), (I-6), (I-7) or (I-8) wherein $R^{1''}$ is $-SiR^7R^8R^9$, either with a fluorine compound such as $(CH_3CH_2CH_2CH_2)_4NF$, CsF, etc. or with hydrochloric acid, acetic acid, citric acid, etc., in an inert solvent. As the inert solvent, THF, acetonitrile, methylene chloride, methanol, ethanol, toluene, water, etc. are used singly or as admixture.

In the case of using the fluorine compound such as $(CH_3CH_2CH_2CH_2)_4NF$, CsF, etc., it is preferred to use a solvent mixture of phosphate buffer or citrate buffer showing a pH value of from 3 to 6 and the aforesaid inert solvent. $(CH_3CH_2CH_2CH_2)_4NF$ or CsF is generally used in 1 to 3 molar equivalents based on Compound (I-1)b, (I-2)a, (I-2)b, (I-3), (I-4), (I-5), (I-6), (I-7) or (I-8). Hydrochloric acid, acetic acid, citric acid, etc. are used in 1 to 30 molar equivalents based on Compound (I-1)b, (I-2)a, (I-2)b, (I-3), (I-4), (I-5), (I-6), (I-7) or (I-8). The reaction is generally carried out at $-20$ to $60°$ C. and completed in 1 to 12 hours.

Furthermore, Compound (I-9) can be obtained by reacting compounds which are Compounds (I-1)b, (I-2)a, (I-2)b, (I-3), (I-4), (I-5), (I-6), (I-7) and (I-8) wherein $R^{1''}$ is $-CH_2OCH_3$ with hydrochloric acid in an inert solvent. As the inert solvent, THF, methanol, ethanol, acetonitrile, dioxane, etc. are used singly or as admixture. Hydrochloric acid is used in 1 to 30 molar equivalents based on Compound (I-1)b, (I-2)a, (I-2)b, (I-3), (I-4), (I-5), (I-6), (I-7) or (I-8). The reaction is generally carried out at 0 to 100° C. and completed in 2 to 20 hours.

Next, processes for producing Compound (II) are described below.

Compounds (II-1)a, (II-1)b, (II-2)a, (II-2)b, (II-3), (II-4), (II-5), (II-6), (II-7), (II-8) and (II-9) can be prepared from DC-89A1 or DC-89B1 through Steps 1 through 9 described above.

DC-89A1 $\xrightarrow{\text{Step 1-a}}$
DC-89B1

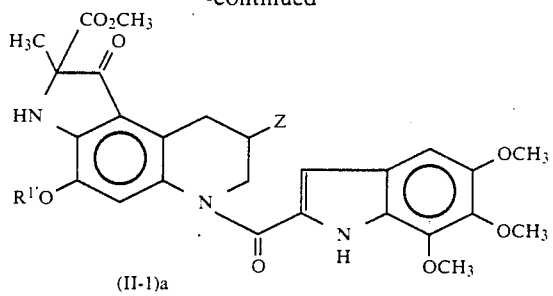

(II-1)a

Compound (II-1)a $\xrightarrow{\text{Step 1-b}}$

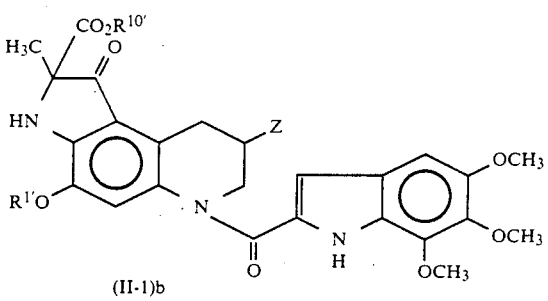

(II-1)b

Compound (II-1)a $\xrightarrow{\text{Step 2-a}}$

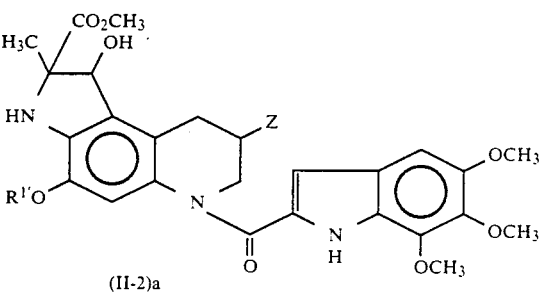

(II-2)a

Compound (II-1)a $\xrightarrow{\text{Step 2-b}}$

-continued

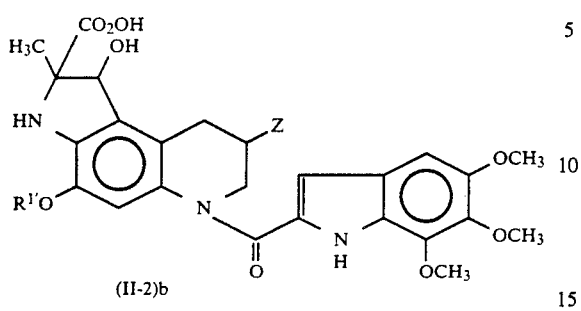
(II-2)b

Compound (II-2)a —Step 3→

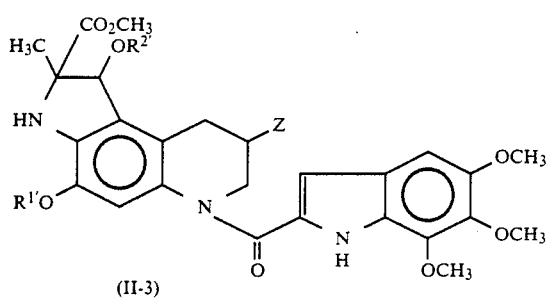
(II-3)

Compound (II-2)b —Step 4→

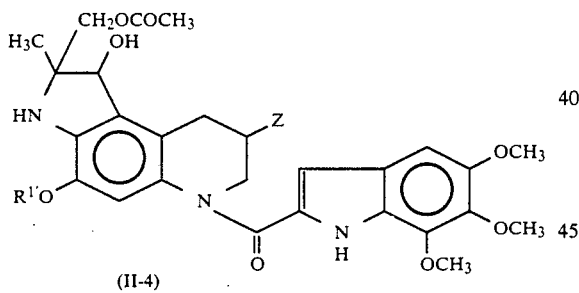
(II-4)

Compound (II-1)a —Step 5→

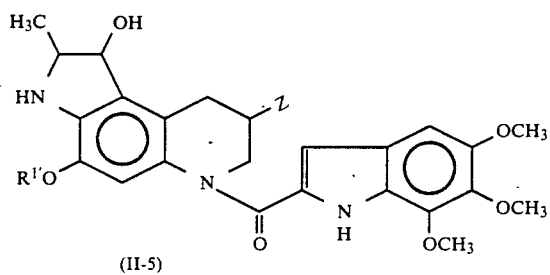
(II-5)

Compound (II-2)b
Compound (II-4) —Step 6→
Compound (II-5)

-continued

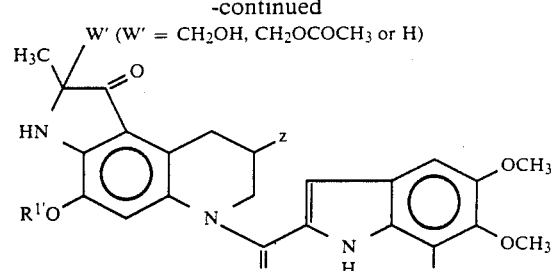
(II-6)

Compound (II-1)c —Step 7→

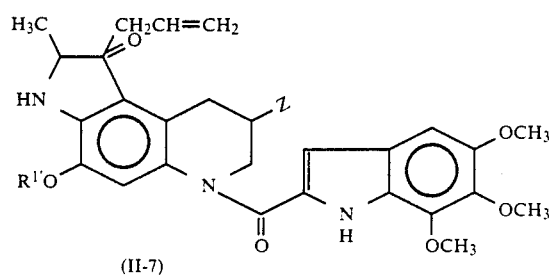
(II-7)

Compound (II-1)a —Step 8→

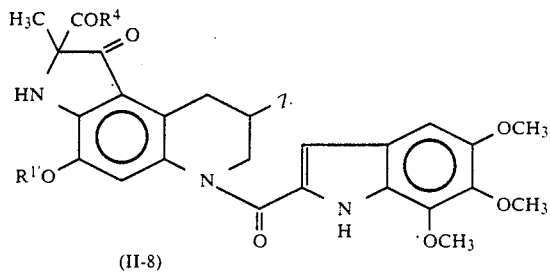
(II-8)

Compound (II-1)b, (II-2)a, (II-2)b,
(II-3), (II-4), (II-5), —Step 9→
(II-6), (II-7), (II-8)

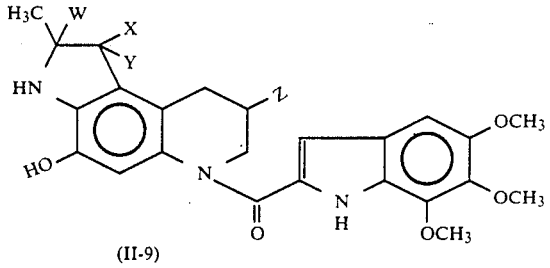
(II-9)

Next, processes for synthesis of Compound (III) are described below.

Compound (III) can be prepared by reacting Compound (I-9) or Compound (II-9) which is Compound (I) or Compound (II) wherein $R^1$ is hydrogen with a base in an insert solvent.

Compound (I-9) —Step 10→
(II-9)

-continued

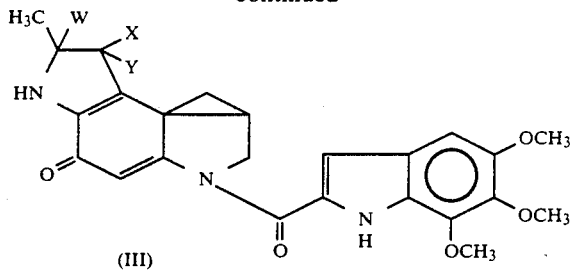

As the inert solvent, acetonitrile, DMF, methylene chloride, THF, dimethyl sulfoxide, etc. are used singly or as admixture. As the base, triethylamine, diisopropylethylamine, potassium t-butoxide, 1,8-diazabicyclo[5.4.0]undeca-7-ene, potassium carbonate, sodium hydride, etc. may be generally used in 1 to 2 molar equivalents based on Compound (I-9) or Compound (II-9) The reaction is generally carried out at −20 to 50° C. and completed in 10 minutes to 5 hours.

Compound (III) can be prepared in a manner similar to Step 9 except that compounds which are Compounds (I-1)b, (I-2)a, (I-2)b, (I-3), (I-4), (I-5), (I-6), (I-7), (I-8), (II-1)b, (II-2)a, (II-2)b, (II-3), (II-4), (II-5), (II-6), (II-7) and (II-8) wherein $R^{1'}$ is $-SiR^7R^8R^9$ are reacted with fluorine compounds in the absence of a buffer showing a pH value of from 3 to 6.

If necessary, water, a buffer, hydrochloric acid, etc. are added to the reaction solution, after completion of the reaction to stop the reaction The reaction mixture is then extracted with a non-aqueous solvent such as ethyl acetate, chloroform, diethyl ether, etc. After washing with water, sodium hydrogencarbonate aqueous solution, saturated sodium chloride aqueous solution, etc., the extract is dried over anhydrous sodium sulfate, etc. and the solvent is then distilled off. Alternatively, the reaction solution is concentrated as it is and purified by column chromatography using silica gel, thin layer chromatography, preparative high performance liquid chromatography, recrystallization, etc.

Structures and compound numbers of representative compounds which fall under Compound (I), Compound (II) and Compound (III) are shown in Table 1. In Table 1, types (I), (II) and (III) indicate that they fall within Compound (I), Compound (II) and Compound (III), respectively.

TABLE 1

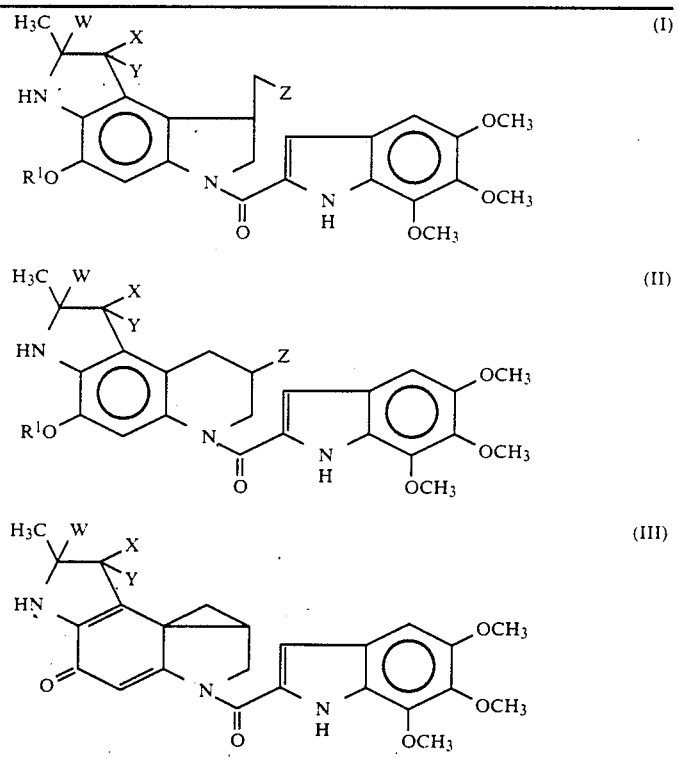

| Compound | Type | W | X | Y | Z | $R^1$ |
|---|---|---|---|---|---|---|
| 1 | I | $CO_2CH_3$ | | =O | Br | $(CH_3)_3CSi(CH_3)_2$ |
| 2 | I | $CO_2CH_3$ | | =O | Br | $CH_2OCH_3$ |
| 3* | I | $CO_2CH_3$ | H | OH | Br | $(CH_3)_3CSi(CH_3)_2$ |
| 4* | I | $CO_2CH_3$ | OH | H | Br | $(CH_3)_3CSi(CH_3)_2$ |
| 5** | I | $CO_2CH_3$ | H | OH | Br | H |
| 6* | I | $CO_2CH_3$ | OH | H | Br | H |
| 7 | I | $CO_2CH_3$ | | =O | Br | $COCH_3$ |
| 8 | I | $CO_2CH_3$ | H | $OCOCH_3$ | Br | $(CH_3)_3CSi(CH_3)_2$ |
| 9 | I | $CO_2CH_3$ | | =O | Br | $CH_3$ |
| 10* | I | $CO_2CH_3$ | H | OH | Br | $CH_3$ |
| 11* | I | $CO_2CH_3$ | OH | H | Br | $CH_3$ |
| 12 | I | $CO_2CH_3$ | H | $OCH_3$ | Br | $CH_3$ |
| 13 | I | $CO_2CH_3$ | | =O | Br | $\overset{\parallel}{\underset{O}{C}}N(CH_3)_2$ |

TABLE 1-continued

| | | | | | |
|---|---|---|---|---|---|
| 14 | I | $CO_2CH_3$ | =O | Br | $\underset{\underset{O}{\|\|}}{C}OCH_2CH=CH_2$ |
| 15 | I | $CO_2CH_3$ | =O | Br | $\underset{\underset{O}{\|\|}}{C}(CH_2)_{10}CH_3$ |
| 16 | I | $CO_2C_2H_5$ | =O | Br | $(CH_3)_3CSi(CH_3)_2$ |
| 17 | I | $CO_2C_2H_5$ | =O | Br | H |
| 18 | I | $CO_2CH_2CH=CH_2$ | =O | Br | $(CH_3)_3CSi(CH_3)_2$ |
| 19 | I | $CO_2CH_2CH=CH_2$ | =O | Br | H |
| 20 | III | $CO_2CH_2CH=CH_2$ | =O | — | — |
| 21 | I | $CO_2CH_2Ph$** | =O | Br | H |
| 22 | I | $CO_2CH_2CH_2OH$ | =O | Br | $(CH_3)_3CSi(CH_3)_2$ |
| 23 | I | $CO_2CH_2CH_2OH$ | =O | Br | H |
| 24 | I | $CH_2CH=CH_2$ | =O | Br | $(CH_3)_3CSi(CH_3)_2$ |
| 25 | I | $CH_2CH=CH_2$ | =O | Br | H |
| 26 | I | $CH_2OH$ | H   OH | Br | $(CH_3)_3CSi(CH_3)_2$ |
| 27 | I | $CH_2OCOCH_3$ | H   OH | Br | H |
| 28 | I | $CH_2OH$ | =O | Br | $(CH_3)_3CSi(CH_3)_2$ |
| 29 | I | $CH_2OH$ | =O | Br | H |
| 30 | I | H | H   OH | Br | $(CH_3)_3CSi(CH_3)_2$ |
| 31 | I | $CO(CH_2)_3CH_3$ | =O | Br | $(CH_3)_3CSi(CH_3)_2$ |
| 32 | I | $CO(CH_2)_3CH_3$ | =O | Br | H |
| 33 | II | $CO_2CH_3$ | =O | Br | $\underset{\underset{O}{\|\|}}{C}N(CH_3)_2$ |

Note
*Compound Nos. 3 and 4, Compound Nos. 5 and 6, and Compound Nos. 10 and 11 are steric isomers.
**Ph represents phenyl.

Next, the pharmacological activity of Compound (I), Compound (II) and Compound (III) is described in the following experiment.

Experiment

The pharmacological activity of Compound (I), Compound (II) and Compound (III) was determined by growth inhibition test using HeLa $S_3$ cells.

Test on growth inhibition of HeLa $S_3$ cells:

HeLa $S_3$ cells diluted to $3 \times 10^4$ cells/ml with MEM medium containing 10% calf fetal serum and 2 mM glutamine were separately distributed by 0.1 ml each in each well of a 96 well microtiter plate.

After culturing at 37° C. overnight in a $CO_2$ incubator, 0.05 ml each of a test sample appropriately diluted with MEM medium was added to each well.

After culturing the cells for 72 hours in the $CO_2$ incubator, the culture supernatant was removed. After washing once with phosphate buffered physiological saline (PBS), 0.1 ml each of MEM medium containing 0.02% neutral red was added to each well and then cultured at 37° C. for an hour in the $CO_2$-incubator to stain the cells. After removing the culture supernatant, the cells were washed once with physiological saline, and the dye was extracted with 0.001 N HCl/30% ethanol. Absorbance at 550 nm of the extract was measured with a microplate reader. By comparing absorbance of extract of intact cells with that of the cells treated with a test compound in known concentrations $IC_{50}$, i.e. the concentration which inhibited growth of the cells by 50% was determined.

$IC_{50}$ values of representative compounds of Compound (I), Compound (II) and Compound (III) are shown in Table 2.

TABLE 2

| Compound | $IC_{50}$ (nM) |
|---|---|
| 1 | 0.010 |
| 5 | 0.26 |
| 6 | 0.20 |
| 7 | 0.0086 |

TABLE 2-continued

| Compound | $IC_{50}$ (nM) |
|---|---|
| 14 | 0.14 |
| 15 | 0.042 |
| 17 | 0.019 |
| 19 | 0.94 |
| 21 | 1.9 |
| 25 | 0.29 |
| 27 | 3.3 |
| DC-88A | 0.039 |
| DC-89B$_2$ | 0.014 |

Acute Toxicity Test

Using dd strain male mice weighing 20 ±1 g, a test compound was intraperitoneally administered. MLD (the minimum lethal dose) was determined by observing the mortality for 14 days after administration.

The results are shown in Table 3.

TABLE 3

| Compound No. | Acute Toxicity (MLD) mg/kg |
|---|---|
| 1 | 0.25 |
| 5 | 0.63 |
| 6 | 1.3 |
| 7 | 0.063 |
| 8 | 2.5 |
| 13 | 2.5 |
| 14 | 0.5 |
| 15 | 0.5 |

Compound (I), Compound (II) and Compound (III) may be used as antitumor agents singly or generally together with at least one pharmacologically acceptable carriers. For example, Compound (I), Compound (II) and Compound (III) are dissolved in a physiological saline solution or in an aqueous solution of glucose, lactose, mannitol, etc. to prepare a suitable pharmaceutical composition for injection. Alternatively, Compound (I), Compound (II) and Compound (III) are freeze-dried or mixed with sodium chloride to prepare a powdery injection. The pharmaceutical composition may contain additives well known in the art of medical preparation, for example, pharmacologically acceptable salts, etc., if necessary. Although the amount of the compound for dosage varies depending upon age, condition, etc. of the patient, it is suitable to administer the compound in an amount of 0.0001 to 5 mg/kg/day for mammals including human beings. Administration is made once a day (single administration or consecutive administration) or intermittently 1 to 3 times a week or once a 2 to 3 weeks, intravenously. If it is wished, oral administration is also possible in a similar dose through a similar manner. Form of oral administration includes a tablet, a capsule, powders, granules, an ampoule, etc. These preparations contain pharmaceutical aids well known in the art of medical preparation. If it is wished, intraarterial administration, intraperitoneal administration, intrathoracic administration, etc. may also be possible in a similar dose through a similar route.

The antitumor composition of this invention is expected to be effective for leukemia, gastric cancer, colon cancer, lung cancer, breast cancer, uterine cancer, etc. in mammals including human beings.

Certain specific embodiments of the present invention are illustrated by the following examples and reference examples.

Physicochemical properties of the compounds obtained in the following examples and reference examples were determined with the following equipments.

| NMR | JEOL, Ltd. | FX-100 | (100 MHz) |
|---|---|---|---|
| | JEOL, Ltd. | PS-100 | (100 MHz) |
| | Bruker | AM-400 | (400 MHz) |
| MS | Hitachi Ltd. | M-80B | |
| | Shimadzu | QP-1000 | |
| IR | Nippon Bunko | IR-810 | |

As silica gel, Wakogel C-200 ® manufactured by WAKO Pure Chemical Industry Co., Ltd. was used.

Example 1

Synthesis of Compound 1

In 3.0 ml of DMF were dissolved 123 mg of DC-89B2 obtained in Reference Example 2 and 43 mg of imidazole. While cooling at 0° C., 50 mg of t-butyldimethylsilyl chloride was added to the solution. After stirring for 4.5 hours, 2N hydrochloric acid solution was added to the mixture followed by extraction with ethyl acetate. The ethyl acetate layer was washed with aqueous sodium hydrogencarbonate solution and saturated aqueous sodium chloride solution. After drying over anhydrous sodium sulfate, the solvent was distilled off under reduced pressure. The residue was purified by silica gel column chromatography (30 ml; eluted with n-hexane : ethyl acetate =3 : 1) to give 140 mg of Compound 1 (yield, 95%). Physicochemical properties of Compound 1 are shown below.

$^1$H-NMR(400MHz, CDCl$_3$)δ(ppm): 9.38(br s, 1H), 8.23(br
s, 1H), 6.95(d, 1H, J=2.2Hz), 6.87(s, 1H), 5.04
(br, 1H), 4.62(dd, 1H, J=10.6, 9.1Hz), 4.54(dd, 1H, J=0.6, 4.4Hz), 4.17(m, 1H), 4.06(s, 3H), 4.06(dd, 1H, J=10.3, 3.0Hz), 3.99(s, 3H), 3.91
(s, 3H), 3.78(s, 3H), 3.57(dd, 1H, J=9.8, 9.1Hz), 1.69(s, 3H), 1.06(s, 9H), 0.36(s, 3H), 0.35(s, 3H)
IR (KBr) νmax (cm$^{-1}$): 1745, 1700, 1618, 1497, 1293, 837

EXAMPLE 2

Synthesis of Compound 2

In an argon atmosphere, 500 mg (0.85 mmol) of DC-89B2 obtained in Reference Example 2 was dissolved in 20 ml of THF and 41 mg of 60% sodium hydride was added to the solution. After stirring for 5 minutes, 0.16 ml of chloromethyl methyl ether was added to the mixture followed by stirring at 0° C. for 55 minutes. After stirring at room temperature for further 1.5 hours, citrate buffer of pH 4.0 was added to the reaction mixture. The reaction mixture was extracted with ethyl acetate. After washing with saturated aqueous sodium chloride solution, the extract was dried over anhydrous sodium sulfate and the solvent was distilled off under reduced pressure. The residue was purified by silica gel column chromatography (60 ml, eluted with chloroform) to give 502 mg of Compound 2 (yield, 93%).

Physicochemical properties of Compound 2 are as follows.

$^1$H-NMR(400MHz, CDCl$_3$)δ(ppm): 8.51(s, 1H), 6.95(d, 1H,
J=2.3Hz), 6.87(s, 1H), 5.33(d, 1H, J=6.6Hz), 5.31
(d, 1H, J=6.6Hz), 4.62(dd, 1H, J=10.8, 9.4Hz), 4.55(dd, 1H, J=10.8, 4.5Hz), 4.20(m, 1H), 4.06(s, 3H), 4.05(dd, 1H, J=9.9, 3.3Hz), 3.94(s, 3H), 3.91(s, 3H), 3.78(s, 3H), 3.60(dd, 1H, J=9.9, 9.0Hz), 3.56(s, 3H), 1.70(s, 3H)
SIMS m/z: 634, 632 (M+1)$^+$

EXAMPLE 3

Synthesis of Compound 3 and Compound 4

Compound 1, 158 mg, was dissolved in 10 ml of methanol and 8.5 mg of sodium borohydride was added to the solution under cooling at 0° C. After the reaction mixture was stirred for an hour, 6.0 mg of sodium borohydride was further added to the reaction mixture followed by stirring for 30 minutes. The reaction mixture was poured into 2 N hydrochloric acid. The mixture was extracted with chloroform. After washing successively with aqueous sodium hydrogencarbonate solution and saturated aqueous sodium chloride solution, the chloroform layer was dried over anhydrous sodium sulfate. After the solvent was distilled off under reduced pressure, the residue was purified by silica gel column chromatography (100 ml) and eluted with n-hexane : ethyl acetate=3 : 1 to give 64 mg of Compound (yield, 40%). Further, elution was carried out with n-hexane : ethyl acetate=1 : 1 to give 43 mg of Compound 4 (yield 27%).

Physicochemical properties of Compound 3 are as follows.

$^1$H-NMR(CDCl$_3$)δ(ppm): 9.43(br s, 1H), 7.91(br s, 1H),
6.91(d, 1H, J=2.2Hz), 6.86(s, 1H), 5.31(br, 1H), 4.57(dd, 1H, J=10.6, 8.9Hz), 4.50(dd, 1H, J=10.6, 3.9Hz), 4.07(dd, 1H, J=10.3, 3.2Hz), 4.05(s, 3H), 3.93(s, 3H), 3.92(m, 1H), 3.91(s, 3H), 3.72(s, 3H), 3.49(dd, 1H, J=10.1, 9.8Hz), 2.09(br, 1H), 1.60(s, 3H), 1.04(s, 9H), 0.32(s, 3H), 0.30(s, 3H)
SIMS m/z: 706, 704 (M+1)$^+$ Physicochemical properties of Compound 4 are as follows.

$^1$H-NMR(400MHz, CDCl$_3$)δ(ppm): 9.40(br s, 1H), 7.88(br
s, 1H), 6.91(d, 1H, J=2.2Hz), 6.86(s, 1H), 5.08
(br s, 1H), 4.61(dd, 1H, J=10.3, 9.4Hz), 4.44(dd, 1H, J=10.6, 4.9Hz), 4.08(m, 1H), 4.06(s, 3H),
3.93(s, 3H), 3.91(s, 3H), 3.82(dd, 1H, J=10.1, 3.4Hz),
3.79(s, 3H), 3.54(dd, 1H, J=10.1, 9.4Hz),
3.24(br 1H), 1.61(s, 3H), 1.02(s, 9H), 0.30(s,
3H), 0.29(s, 3H)
EIMS m/z: 705, 703 (M+)

EXAMPLE 4

Synthesis of Compound 5

Compound 3, 30 mg was dissolved in 3.5 ml of THF, and 3.0 ml of phosphate buffer of pH 4 and 0.6 ml of 0.1 M tetrabutyl ammonium fluoride-THF solution were added to the solution. The mixture was stirred at room temperature for 5 hours. The reaction mixture was poured into 2 N hydrochloric acid and the mixture was extracted with ethyl acetate. After washing successively with aqueous sodium hydrogencarbonate solution and saturated aqueous sodium chloride solution, the ethyl acetate layer was dried over anhydrous sodium sulfate. After the solvent was distilled off under reduced pressure, the residue was purified by preparative thin layer chromatography (developed with $CHCl_3:CH_3OH=10:1$) to give 19 mg of Compound 5 (yield, 76%). Physicochemical properties of Compound 5 are as follows.

$^1$H-NMR(400MHz, $CDCl_3$)δ(ppm): 9.53(br s, 1H), 8.22(s,
1H), 6.91(s, 1H), 6.85(d, 1H, J=2.2Hz), 5.17(s,
1H), 4.42(dd, 1H, J=10.3, 9.4Hz), 4.15(s, 3H),
4.13(dd, 1H, J=10.6, 3.4Hz), 4.00(s, 3H), 3.96
(s, 3H), 3.94(m, 1H), 3.82(m, 1H), 3.62(s, 3H),
2.96(dd, 1H, J=10.8, 10.8Hz), 1.71(s, 3H)
SIMS m/z : 592, 590 (M+1)+
EIMS m/z : 591, 589 (M+)
IR (KBr) νmax (cm$^{-1}$) 3430, 1735, 1620, 1490, 1308

EXAMPLE 5

Synthesis of Compound 6

Compound 4, 30 mg, was dissolved in 4.0 ml of THF and 3.0 ml of phosphate buffer of pH 4 and 1.1 ml of 0.1M tetrabutyl ammonium fluoride-THF solution. The mixture was stirred at room temperature for 5 hours. The reaction mixture was poured into 2 N hydrochloric acid and the mixture was extracted with ethyl acetate. After washing successively with aqueous sodium hydrogencarbonate solution and saturated aqueous sodium chloride solution, the ethyl acetate layer was dried over anhydrous sodium sulfate After the solvent was distilled off under reduced pressure, the residue was purified by silica gel column chromatography (20 ml, eluted with $CHCl_3$: $CH_3OH=98:2$) to give 24 mg of Compound 6 (yield, 95%).

Physicochemical properties of Compound 6 are as follows.

1H-NMR(400MHz, $CDCl_3$)δ(ppm): 9.54(br s, 1H), 7.80(s,
1H), 6.70(d, 1H, J=2.0Hz), 6.62(s, 1H), 4.11(s,
3H), 4.10(m, 2H), 3.92(s, 3H), 3.86(s, 3H), 3.73
(s, 3H), 3.72(m, 1H), 3.65(dd, 1H, J=10.1, 3.2
Hz), 3.43(dd, 1H, J=10.1, 9.1Hz), 1.56(s, 3H)
SIMS m/z 592, 590 (M+1)+
IR (KBr) νmax (cm$^{-1}$): 3450, 1730, 1620, 1495, 1310

EXAMPLE 6

Synthesis of Compound 7

In 4.0 ml of pyridine was dissolved 190 mg of DC-89B2 obtained in Reference Example 2 and 0.2 ml of acetic anhydride was added to the solution. After stirring for 3.5 hours at 0° C, toluene was added to the reaction mixture. Then the mixture was concentrated under reduced pressure. The residue was purified by silica gel column chromatography (100 ml; eluted with chloroform) to give 189 mg of Compound 7 (yield, 93%). Physicochemical properties of Compound 7 are shown below.

1H-NMR(400MHz, $CDCl_3$)δ(ppm): 9.39(br s, 1H), 8.47(s,
1H), 6.95(d, 1H, J=2.2Hz), 6.87(s, 1H), 5.17(br
s, 1H), 4.64(dd, 1H, J=10.6, 9.3Hz), 4.58(dd, 1H,
J=10.6, 4.4Hz), 4.24(m, 1H), 4.08(s, 3H), 4.05
(dd, 1H, J=9.8, 3.2Hz), 3.94(s, 3H), 3.91(s, 3H),
3.78(s, 3H), 3.61(dd, 1H, J=9.8, 8.9Hz), 2.39
(s, 3H), 1.68(s, 3H)
EIMS m/z : 631, 629 (M+)
IR (KBr) νmax (cm$^{-1}$): 1748, 1700, 1618, 1492, 1309, 1191

EXAMPLE 7

Synthesis of Compound 8

Compound 3, 30 mg, was dissolved in 2.0 ml of pyridine and 0.02 ml of acetic anhydride and 1 mg of dimethylaminopyridine were added to the solution. After the mixture was stirred at room temperature for 100 minutes, the reaction mixture was poured into 2 N hydrochloric acid. The mixture was extracted with chloroform. After washing successively with aqueous sodium hydrogencarbonate solution and saturated aqueous sodium chloride solution, the chloroform layer was dried over anhydrous sodium sulfate. After the solvent was distilled off under reduced pressure, the residue was purified by silica gel column chromatography (20 ml, eluted with n-hexane : ethyl acetate=3 : 1) to give 20 mg of Compound 8 (yield, 63%). Physicochemical properties of Compound 8 are as follows.

$^1$H-NMR(400MHz, $CDCl_3$)δ(ppm): 9.39(br s, 1H), 7.92(br
s, 1H), 6.90(d, 1H, J=2.2Hz), 6.86(s, 1H), 6.72
(s, 1H), 4.52(m, 2H), 4.06(s, 3H), 3.93(s, 3H),
3.91(s, 3H), 3.81(m, 1H), 3.76(s, 3H), 3.51(dd,
1H, J=10.3, 3.2Hz), 3.28(dd, 1H, J=10.1 10.1Hz),
2.19(s, 3H), 1.51(s, 3H), 1.04(s, 9H), 0.33(s,
3H), 0.30(s, 3H)
SIMS m/z : 748, 746 (M+1)+
IR (KBr) νmax (cm$^{-1}$): 1735, 1624, 1490, 1309, 1220, 837

EXAMPLE 8

Synthesis of Compound 9

In 20 ml of methanol was dissolved 45 mg of DC-89B2 obtained in Reference Example 2 and 1 ml of diazomethane ether-solution was added to the solution. Under ice cooling, the mixture was stirred for 30 minutes. The solvent in the reaction mixture was distilled off under reduced pressure to give 45 mg of Compound 9 (yield, 100%).

Physicochemical properties of Compound 9 are shown below. p $^1$H-NMR(400MHz, $CDCl_3$)δ(ppm): 9.37(br s, 1H), 8.29(s, 1H), 6.96(d, 1H, J=2.4Hz), 6.87(s, 1H), 5.25(s,
1H), 4.63(dd, 1H, J=10.8, 9.4Hz), 4.55(dd, 1H,
J=10.8, 4.5Hz), 4.19(m, 1H), 4.07(s, 3H), 4.04
(dd, 1H, J=10.0, 3.3Hz), 3.98(s, 3H), 3.94(s, 3H),
3.91(s, 3H), 3.78(s, 3H), 3.61(dd, 1H, J=10.0,
8.7Hz), 1.69(s, 3H)

EIMS m/z : 603, 601(M+), 521, 370, 368, 288, 234

EXAMPLE 9

Synthesis of Compound 10 and Compound 11

Compound 9, 54 mg, was dissolved in 3 ml of methanol and 12 mg of sodium borohydride was added to the solution. After the mixture was stirred at room temperature for 10 minutes, the reaction mixture was partitioned with ethyl acetate (50 ml)-water (50 ml). The aqueous layer was further extracted twice with 30 ml of ethyl acetate. After washing with saturated aqueous sodium chloride solution, the ethyl acetate layer was dried over anhydrous sodium sulfate. After the solvent was distilled off under reduced pressure, the residue was purified by preparative thin layer chromatography (developed with toluene : acetone=7 : 3) and then by high performance liquid chromatography (ODS column: 8 mm$\phi$×100 mm, eluted with 40% aqueous acetonitrile) to give 19 mg of Compound 10 (yield, 34%) and 8 mg of Compound 11 (yield, Physicochemical properties of Compound 10 are as follows.

$^1$H-NMR(400MHz, CDCl$_3$)$\delta$(ppm): 9.56(br s, 1H), 7.96(s,
1H), 6.91(d, 1H, J=2.3Hz), 6.86(s, 1H), 5.33(br
s, 1H), 4.56(dd, 1H, J=10.7, 8.8Hz), 4.50(dd, 1H,
J=10.7, 4.0Hz), 4.08(dd, 1H, J=10.4, 3.6Hz), 4.06
(s, 3H), 3.93(s, 3H), 3.90(s, 3H), 3.85(s, 3H),
3.71(s, 3H), ca.3.9(m, 1H), 3.45(t, 1H, J=10.4Hz),
2.61(br s, 1H), 1.59(s, 3H)

EIMS m/z : 605, 603(M+), 587, 585, 372, 370, 272, 234

Physicochemical properties of Compound 11 are as follows.

$^1$H-NMR(400MHz, CDCl$_3$)$\delta$(ppm): 9.43(br s, 1H), 7.98(br
s, 1H), 6.90(d, 1H, J=2.3Hz), 6.86(s, 1H), 5.07
(d, 1H, J=8.5Hz), 4.57(dd, 1H, J=10.6, 9.3Hz),
4.43(dd, 1H, J=10.6, 5.0Hz), 4.40(br s, 1H), 4.06
(s, 3H), ca.4.1(m, 1H), 3.94(s, 3H), 3.90(s, 3H),
3.87(s, 3H), 3.81(s, 3H), 3.78(dd, 1H, J=10.3,
3.4Hz), 3.53(dd, 1H, J=10.3, 9.1Hz), 3.19(d, 1H,
J=8.5Hz), 1.59(s, 3H)

EIMS m/z : 605, 603(M+), 587, 585, 372, 370, 272, 234

EXAMPLE 10

Synthesis of Compound 12

Compound 10, 24 mg, was dissolved in 0.5 ml of DMF and 40 μl of methyl iodide was added to the solution in the presence of 40 mg of silver oxide. The reaction mixture was stirred for 8 hours while keeping the reaction mixture from light. After the reaction mixture was diluted with 20 ml of methanol, solids were filtered off. The solvent was distilled off under reduced pressure. The resulting residue was purified by high performance liquid chromatography (ODS column: 8 mm$\phi$×100 mm, eluted with 70% aqueous acetonitrile) to give 3 mg of Compound 12 (yield, 12%) as yellow powders.

Physicochemical properties of Compound 12 are as follows.

EIMS m/z : 619, 617(M+), 386, 384, 327, 325, 286, 234

EXAMPLE 11

Synthesis of Compound 13

In 5 ml of pyridine was dissolved 101 mg of DC-89B2 obtained in Reference Example 2 and 3 mg of dimethylaminopyridine and 0.1 ml of dimethylcarbamyl chloride were added to the solution. After stirring at room temperature overnight, the reaction mixture was poured into 2 N hydrochloric acid and extracted with chloroform. After washing successively with aqueous sodium hydrogencarbonate solution and saturated aqueous sodium chloride solution, the chloroform layer was dried over anhydrous sodium sulfate. After the solvent was distilled off under reduced pressure, the residue was purified by silica gel column chromatography (50 ml; eluted with chloroform) to give 64 mg of Compound 13 (yield, 57%).

Physicochemical properties of Compound 13 are shown below.

$^1$H-NMR(400MHz, CDCl$_3$)$\delta$(ppm): 9.35(br s, 1H), 8.44(s,
1H), 6.96(d, 1H, J=2.5Hz), 6.87(s, 1H), 5.53(s,
1H), 4.64(dd, 1H, J=10.8, 9.1Hz), 4.59(dd, 1H,
J=10.8, 4.7Hz), 4.25(m, 1H), 4.08(s, 3H), 4.05
(dd, 1H, J=10.1, 3.4Hz), 3.94(s, 3H), 3.91(s, 3H),
3.78(s, 3H), 3.60(dd, 1H, J=9.8, 8.9Hz), 3.16(s,
3H), 3.06(s, 3H), 1.68(s, 3H)

SIMS m/z : 661, 659(M+1)+

IR (KBr) $\nu$max (cm$^{-1}$) : 1717, 1619, 1495, 1308, 1164

EXAMPLE 12

Synthesis of Compound 14

In 2 ml of pyridine and 1 ml of chloroform was dissolved 200 mg of DC-89B2 obtained in Reference Example 2 and 20 mg of dimethylaminopyridine and 0.3 ml of allyl chloroformate were added to the solution. After stirring at room temperature overnight, the reaction mixture was treated in a manner similar to Example 11 to give 149 mg of Compound 14 (yield, 65%).

Physicochemical properties of Compound 14 are shown below.

$^1$H-NMR(400MHz, CDCl$_3$)$\delta$(ppm): 9.38(br s, 1H), 8.60(s,
1H), 6.95(s, 1H, J=2.2Hz), 6.86(s, 1H), 6.02(ddt,
1H, J=17.2, 10.6, 5.9Hz), 5.47(ddd, 1H, J=17.2,
2.7, 1.5Hz), 5.38(ddd, 1H, J=10.3, 2.2, 1.2Hz),
5.32(br s, 1H), 4.80(ddd, 2H, J=5.9, 1.2, 1.2Hz),
4.65(dd, 1H, J=10.8, 9.6Hz), 4.58(dd, 1H, J=10.8,
4.7Hz), 4.24(m, 1H), 4.07(s, 3H), 4.04(dd, 1H,
J=10.3, 3.2Hz), 3.94(s, 3H), 3.91(s, 3H), 3.78(s,
3H), 3.62(dd, 1H, J=10.1, 8.9Hz), 1.69(s, 3H)

SIMS m/z : 674, 672 (M+1)+

IR (KBr) $\nu$max (cm$^{-1}$): 1745, 1701, 1619, 1493, 1307, 1223

EXAMPLE 13

Synthesis of Compound 15

In 3 ml of pyridine was dissolved 106 mg of DC89B2 obtained in Reference Example 2 and 5 mg of dimethylaminopyridine and 0.24 ml of dodecanoyl chloride were added to the solution. After stirring at room temperature overnight, the reaction mixture was treated in a manner similar to Example 11 to give 84 mg of Compound 15 (yield, 61%).

Physicochemical properties of Compound 15 are shown below.

$^1$H-NMR(400MHz, CDCl$_3$)δ(ppm): 9.41(br s, 1H), 8.46(s,

1H), 6.95(d, 1H, J=2.2Hz), 6.87(s, 1H), 5.15(br s, 1H), 4.64(dd, 1H, J=10.8, 9.4Hz), 4.58(dd, 1H, J=10.8, 4.4Hz), 4.24(m, 1H), 4.07(s, 3H), 4.04 (dd, 1H, J=10.3, 3.2Hz),3.94(s, 3H), 3.91(s, 3H), 3.78(s, 3H), 3.61(dd, 1H, J=10.1, 8.9Hz), 2.63 (t, 2H, J=7.6Hz), 1.79(m, 2H), 1.68(s, 3H), 1.45–1.20(m, 16H), 0.88(t, 3H, J=6.9Hz)

SIMS m/z : 772, 770 (M+1)$^+$

IR (KBr) νmax (cm$^{-1}$) 2928, 2854, 1740, 1699, 1616

EXAMPLE 14

Synthesis of Compound 16 and Compound 17

Compound 1, 40 mg, obtained in Example 1 was dissolved in 15 ml of ethanol. Under cooling at 0° C., 8 mg of potassium carbonate was added to the solution. The mixture was stirred for 160 minutes. The reaction mixture was poured into 2 N hydrochloric acid and extracted with chloroform. After washing successively with aqueous sodium hydrogencarbonate solution and saturated aqueous sodium chloride solution, the chloroform layer was dried over anhydrous sodium sulfate. The solvent was distilled off under reduced pressure to give crude Compound 16.

The crude product of Compound 16 obtained was dissolved in 4.0 ml of THF and 4.0 ml of phosphate buffer of pH 4 and 0.56 ml of 0.1 M tetrabutyl ammonium fluoride-THF solution were added to the solution. The mixture was stirred at room temperature for 3 hours. The reaction mixture was poured into 2 N hydrochloric acid and the mixture was extracted with ethyl acetate. AFter washing successively with aqueous sodium hydrogencarbonate solution and saturated aqueous sodium chloride solution, the ethyl acetate layer was dried over anhydrous sodium sulfate. After the solvent was distilled off under reduced pressure, the residue was purified by silica gel column chromatography (20 ml, eluted with chloroform : methanol=98 : 2) to give 25 mg of Compound 17 (yield, 75%).

Physicochemical properties of Compound 16 are as follows.

$^1$H-NMR(100MHz, CDCl$_3$)δ(ppm): 9.30(br s, 1H), 8.25(s,

1H), 7.10(d, 1H, J=2.2Hz), 6.91(s, 1H), 5.10(br s, 1H), 4.25(q, 2H, J=7Hz), 4.10(s, 3H), 3.95(s, 3H), 3.90s, 3H), 1.72(s, 3H), 1.28(t, 3H, J=7Hz), 1.05(s, 9H), 0.35(s, 6H)

Physicochemical properties of Compound 17 are as follows.

$^1$H-NMR(400MHz, CDCl$_3$)δ(ppm): 9.63(br s, 1H), 9.54(br s, 1H), 8.49(s,1H), 6.99(d, 1H, J=2.2Hz), 6.85 (s, 1H), 4.61(dd, 1H, J=10.8, 9.3Hz), 4.53(dd, 1H, J=11.1, 4.4Hz), 4.21(m, 2H), 4.19(m, 1H), 4.14(s, 3H), 4.02(dd, 1H, J=9.8, 3.4Hz), 3.96(s, 3H), 3.91(s, 3H), 3.58(dd, H, J=9.8, 8.9Hz), 1.70(s, 3H), 1.26(t, 3H, J=7.1Hz)

EIMS m/z : 603, 601(M$^+$)

IR (KBr) νmax (cm$^{-1}$): 3405, 1718, 1700, 1614, 1497, 1305

EXAMPLE 15

Synthesis of Compound 18 and Compound 19

Compound 1, 120 mg, was dissolved in 5.7 ml of allyl alcohol and 22 mg of potassium carbonate was added to the solution followed by stirring for 5 hours at 0° C. The reaction mixture was poured into 2 N hydrochloric acid and extracted with ethyl acetate. After washing successively with aqueous sodium hydrogencarbonate solution and saturated aqueous sodium chloride solution, the ethyl acetate layer was dried over anhydrous sodium sulfate. The solvent was distilled off under reduced pressure and the residue was purified by silica gel column chromatography (100 ml) and eluted with n-hexane : ethyl acetate =3 : 1 to gibe 105 mg of Compound 18 (yield, 84%). Further, elution was carried out with n-hexane : ethyl acetate =1 : 2 to give 12 mg of Compound 19 (yield, 11%).

Physicochemical properties of Compound 18 are as follows.

$^1$H-NMR(100MHz, CDCl$_3$)δ(ppm): 9.40(br s, 1H), 8.30(s,

1H), 7.00(br s, 1H), 6.90(s, 1H), 5.90(m, 1H), 5.5–5.1(m, 3H), 4.7–4.5(m, 4H), 4.10(s, 3H), 3.95 (s, 3H), 3.90(s, 3H), 3.60(m, 1H), 1.70(s. 3H), 1.05(s, 9H), 0.35(s, 6H)

SIMS m/z : 730, 728(M+1)$^+$

Physicochemical properties of Compound 19 are as follows.

$^1$H-NMR(400MHz, CDCl$_3$)δ(ppm): 9.73(br s, 1H), 9.52(br s, 1H), 8.50(s, 1H), 7.00(d, 1H, J=2.2Hz), 6.86 (s, 1H), 5.87(ddt, 1H, J=17.2, 10.3, 5.4Hz), 5.42 (br s, 1H), 5.36(dd, 1H, J=17.2, 1.5Hz), 5.23(dd, 1H, J=10.3, 1.2Hz), 4.64(m, 2H), 4.62(dd, 1H, J=10.8, 10.8Hz), 4.54(dd, 1H, J=10.8, 4.2Hz), 4.18(m, 1H), 4.14(s, 3H), 4.03(dd, 1H, J=10.1, 3.2Hz), 3.96(s, 3H), 3.92(s, 3H), 3.59(dd, 1H, J=10.1, 8.9Hz), 1.72(s, 3H)

EIMS m/z: 615, 613(M$^+$)

IR (KBr) νmax (cm$^{-1}$): 3370, 1739, 1699, 1611, 1502, 1307

EXAMPLE 16

Synthesis of Compound 20

Compound 18, 23 mg, was dissolved in 3.0 ml of THF and 8.0 mg of benzyltrimethyl ammonium fluoride was added to the solution under ice cooling at 0° C. followed by stirring at room temperature for 4.5 hours. The reaction mixture was poured into 2 N hydrochloric acid and extracted with chloroform. After washing successively with aqueous sodium hydrogencarbonate solution and saturated aqueous sodium chloride solution, the chloroform layer was dried over anhydrous sodium sulfate. The solvent was distilled off under reduced pressure and the residue was purified by silica gel column chromatography (100 ml, eluted with chloroform : acetone=50 : 1) to give 8.2 mg of Compound 20 (yield, 48%).

Physicochemical properties of Compound 20 are as follows.

$^1$H-NMR(400MHz, CDCl$_3$)δ(ppm): 9.25(br, s, 1H), 7.17(s,

1H), 6.94(d, 1H, J=2.2Hz), 6.78(s, 1H), 6.04(br s, 1H), 5.88(ddt, 1H, J=17.2, 10.3, 5.7Hz), 5.32 (ddd, 1H, J=17.2, 3.0, 1.5Hz), 5.25(ddd, 1H, J=10.3, 2.5, 1.2Hz), 4.64(ddd, 1H, J=5.7, 1.5, 1.2

Hz), 4.45(dd, 1H, J=10.3, 4.8Hz), 4.41(d, 1H, J= 4.7Hz), 4.08(s, 3H), 3.94(s, 3H), 3.89(s, 3H), 2.25(dd, 1H, J=7.6, 3.9Hz), 1.68(s, 3H), 1.28(dd, 1H, J=4.7, 4.2Hz)
EIMS m/z: 533(M+)
IR (KBr) $\nu$max (cm$^{-1}$): 3300, 1741, 1680, 1631, 1385

EXAMPLE 17

Synthesis of Compound 21

In 3.0 ml of chloroform was dissolved 47 mg of Compound 1 and 1.0 ml of benzyl alcohol and 17 mg of potassium carbonate were added to the solution at 0° C. under ice cooling. After stirring at room temperature for 2 days, the reaction mixture was treated in a manner similar to Example 14 to give 24 mg of Compound 21 (yield, 57%).

Physicochemical properties of Compound 21 are shown below.

$^1$H-NMR(400MHz, CDCl$_3$)$\delta$(ppm): 9.83(br s, 1H), 9.55(br
  s, 1H), 8.48(s, 1H), 7.29(m, 5H), 6.97(d, 1H, J=
  2.5Hz), 6.83(s, 1H), 5.49(br s, 1H), 5.21(d, 1H,
  J=12.5Hz), 5.10(d, 1H, J=12.5Hz), 4.57(dd, 1H,
  J=10.8, 9.3Hz), 4.51(dd, 1H, J=10.8, 4.2Hz), 4.14
  (m, 1H), 4.07(s, 3H), 4.00(dd, 1H, J=10.1, 3.2Hz),
  3.94(s, 3H), 3.91(s, 3H), 3.57(dd, 1H, J=10.1,
  9.1Hz), 1.71(s, 3H)
EIMS m/z: 665, 663(M+)
IR (KBr) $\nu$max (cm$^{-1}$) : 3370, 1733, 1692, 1610, 1499, 1307

EXAMPLE 18

Synthesis of Compound 22 and Compound 23

Compound 1, 23 mg, was dissolved in 0.5 ml of chloroform. Under cooling at 0° C., 0.5 ml of THF, 0.5 ml of ethylene glycol and 4.2 mg of potassium carbonate were added to the solution. The mixture was stirred for 5 hours. The reaction mixture was poured into 2 N hydrochloric acid and extracted with ethyl acetate. After washing successively with aqueous sodium hydrogencarbonate solution and saturated aqueous sodium chloride solution, the ethyl acetate layer was dried over anhydrous sodium sulfate. The solvent was distilled off under reduced pressure and the residue was purified by preparative thin layer chromatography (developed with n-hexane : ethyl acetate =1 : 1) to give 7.0 mg of Compound 22 (yield, 29%).

The obtained Compound 22, 7.0 mg, was dissolved in 1.5 ml of THF and 1.2 ml of phosphate buffer of pH 4 and 0.05 ml of 0.1 M tetrabutyl ammonium fluoride-THF solution were added to the solution. The mixture was stirred at 0° C. for 80 minutes. The reaction mixture was then treated in a manner similar to Example 14 to give 3.6 mg of Compound 23 (yield, 61%). Purification was performed by preparative thin layer chromatography (developed with chloroform : methanol =97 : 3).

Physicochemical properties of Compound 22 are as follows.

$^1$H-NMR(100MHz, CDCl$_3$)$\delta$(ppm): 9.36(br s, 1H), 8.24(s,
  1H), 6.92(d, 1H, J=2.2Hz), 6.86(s, 1H), 5.08(s,
  1H), 4.7-3.6(m, 9H), 4.05(s, 3H), 3.94(s, 3H),
  3.90(s, 3H), 1.72(s, 3H), 1.05(s, 9H), 0.35(s, 6H)

Physicochemical properties of Compound 23 are as follows.

$^1$H-NMR(400MHz, CDCl$_3$)$\delta$(ppm): 10.23(br s, 1H), 9.43(br
  s, 1H), 8.27(s, 1H), 6.96(d, 1H, J=2.2Hz), 6.74
  (s, 1H), 5.88(br s, 1H), 4.49(m, 1H), 4.42(dd, 1H,
  J=10.6, 9.6Hz), 4.36(dd, 1H, J=10.8, 4.2Hz), 4.26
  (m, 1H), 4.08(s, 3H), 3.93(s, 3H), 3.92-3.87(m,
  3H), 3.84(dd, 1H, J=10.3, 3.2Hz), 3.70(br s, 1H),
  3 55(dd, 1H, J=10.1, 8.1Hz), 1.73(s, 3H)
SIMS m/z 620, 618(M+1)+
IR (KBr) $\nu$max (cm$^{-1}$): 3400, 1734, 1685, 1502, 1308

EXAMPLE 19

Synthesis of Compound 24 and Compound

In 1.5 ml of methylene chloride were dissolved 3.2 mg of tetrakis-triphenylphosphine palladium and 1.4 mg of triphenyl phosphine, and 1.5 ml of a methylene chloride solution containing 20 mg of Compound 18 was added to the solution at 0° C. under cooling. The mixture was stirred for 45 minutes. Chloroform was added to the reaction mixture followed aqueous sodium chloride solution. After the chloroform layer was dried over an hydrous sodium sulfate, the solvent was distilled off under reduced pressure to give crude product of Compound 24.

The obtained crude product of Compound 24 was dissolved in 4.0 ml of THF and 3.0 ml of phosphate buffer of pH 4 and 0.3 ml of 0.1 M tetrabutyl ammonium fluoride were added to the solution. The mixture was stirred at room temperature for 45 minutes. The reaction mixture was then treated in a manner similar to Example 14 to give 9.5 mg of Compound 25 (yield, 62%). Compounds 24 and 25 were both mixtures of stereoisomers.

Physicochemical properties of Compound 24 are as follows.

$^1$H-NMR(100MHz, CDCl$_3$)$\delta$(ppm): 9.44(br s, 1H), 8.23(s,
  1H), 6.96(d, 1H, J=2.2Hz), 6.90(s, 1H), 5.70(m,
  1H), 5.3-5.0(m, 2H), 4.56(m, 2H), 4.3-3.6(m, 3H),
  4.05(s, 3H), 3.96(s, 3H), 3.92(s, 3H), 2.40(m,
  2H), 1.36(s, 3H), 1.05(s, 9H), 0.36(s, 6H)

Physicochemical properties of Compound 25 are as follows.

$^1$H-NMR(400MHz, CDCl$_3$)$\delta$(ppm): 9.75(br s, 1H), 9.50(br
  s, 1H), 8.50(s, 1H), 1b 7.03(d, 1H, J=2.5Hz), 6.89
  (s, 1H), 5.73(m, 1H), 5.14(br d, 1H, J=17.0Hz),
  5.08(br d, 1H, J=10.1Hz), 4.63(dd, 1H, J=11.1,
  9.3Hz), 4.54(m, 1H), 4.21(m, 1H), 4.15(s, 3H),
  4.09(dd, 0.3H, J=10.9, 3.4Hz), 4.05(dd, 0.7H, J=
  10.1, 3.5Hz), 3.97(s, 3H), 3.92(s, 3H), 3.64(dd,
  0.7H, J=8.9, 3.7Hz), 3.60(dd, 0.3H, J=9.8, 9.1Hz),
  2 42(m, 2H), 1.36(s, 0.9H), 1.35(s, 2.1H)
EIMS m/z: 571, 569 (M+)
IR (KBr) $\nu$max (cm$^{-1}$): 3400, 1685, 1610, 1508, 1310

EXAMPLE 20

Synthesis of Compound 26

Compound 1, 198 mg, was dissolved in 17 ml of diethyl ether and 27 mg of lithium aluminum hydride was added to the solution at 0° C. under cooling followed by stirring for 160 minutes. 2 N Hydrochloric acid was added to the reaction mixture and insoluble matters were filtered off. After the filtrate was concentrated, the residue was purified by silica gel column chromatography (100 ml, eluted with chloroform.: methanol =99 : 1) to give 77 mg of Compound 26 (yield, 40%).

Physicochemical properties of Compound 26 are as follows.

$^1$H-NMR(100MHz, CDCl$_3$)$\delta$(ppm): 9.50(br s, 1H), 7.90(s,

1H), 6.95(d, 1H, J=2.0Hz), 6.90(s, 1H), 5.10(d, 1H, J=7.5Hz), 4.60(m, 2H), 4.3–3.8(m, 2H), 4.10 (s, 3H), 3.95(s, 3H), 3.91(s, 3H), 3.52(m, 3H), 2.10(m, 2H), 1.35(s, 3H), 1.05(s, 9H), 0.35(s, 6H)

SIMS m/z: 678, 676 (M+1)$^+$

IR (KBr) $\nu$max (cm$^{-1}$): 3400, 1619, 1473, 1313, 839

EXAMPLE 21

Synthesis of Compound 27

Compound 11, 17 mg, was dissolved in 2.5 ml of pyridine and 0.1 ml of acetic anhydride was added to the solution. The mixture was stirred at room temperature for 3.5 hours. The reaction mixture was poured into 2 N hydrochloric acid and extracted with chloroform. After washing successively with aqueous sodium hydrogencarbonate solution and saturated aqueous sodium chloride solution, the chloroform layer was dried over anhydrous sodium sulfate. The solvent was distilled off under reduced pressure. Then the residue was dissolved in 3.0 ml of THF, and 1.0 ml of phosphate buffer of pH 4 and 0.5 ml of 0.1 M tetrabutyl ammonium fluoride were added to the solution. The mixture was stirred at room temperature for 14 hours. The reaction mixture was treated in a manner similar to Example 14 to Physicochemical properties of Compound 27 are as follows.

$^1$H-NMR(400MHz, CDCl$_3$)$\delta$(ppm): 9.58(br s, 1H), 8.12(br s, 1H), 6.88(br s, 2H), 4.68(br s, 1H), 4.47(dd, 1H, J=10.3, 8.9Hz), 4.19(dd, 1H, J=10.3, 3.2Hz), 4.12(s, 3H), 4.11(m, 1H), 3.97(s, 3H), 3.94(s, 3H), 3.90(d, 1H, J=10.8Hz), 3.85(m, 1H), 3.83(d, 1H, J=11.1Hz), 3.45(br s, 1H), 3.14(dd, 1H, J=10.6, 10.6Hz), 2.03(s, 3H), 1.5(s, 3H)

SIMS m/z: 606, 604 (M+1)$^+$

IR (KBr) $\nu$max (cm$^{-1}$): 3400, 1718, 1619, 1491, 1310

EXAMPLE 22

Synthesis of Compound 28 and Compound 29

Compound 11, 31 mg, was dissolved in 1.5 ml of diethyl ether and 57 mg of manganese dioxide was added to the solution. The mixture was stirred at room temperature for 26 hours. Insoluble matters were removed from the reaction mixture by filtration. After the solvent was distilled off under reduced pressure, the residue was purified by preparative thin layer chromatography (developed with n-hexane : ethyl acetate =2 : 1) to give 3 mg of Compound 28 (yield, 10%).

Compound 28, 4.5 mg, was dissolved in 1.2 ml of THF and, 1.0 ml of phosphate buffer of pH 4 and 0.07 ml of 0.1 M tetrabutyl ammonium fluoride-THF solution were added to the solution. The mixture was stirred at 0° C. for 4.5 hours. The reaction mixture was treated in a manner similar to Example 14 to give 1.9 mg of Compound 29 (yield, 51%).

Physicochemical properties of Compound 28 are as follows.

$^1$H-NMR(400MHz, CDCl$_3$)$\delta$(ppm): 9.39(br s, 1H), 8.23(s,

1H), 6.95(d, 1H, J=2.3Hz), 6.87(s, 1H), 4.62(dd, 1H, J=10.8, 9.3Hz), 4.53(dd, 1H, J=10.8, 4.5Hz), 4.49(br s, 1H), 4.19(m, 1H), 4.06(s, 3H), 4.05(dd, 1H, J=10.1, 3.3Hz), 3.94(s, 3H), 3.91(s, 3H), 3.76(m, 1H), 3.66(br d, 1H, J=10.1Hz), 3.61(dd, 1H, J=10.0, 8.9Hz), 2.14(br, 1H), 1.39(s, 3H), 1.05(s, 3H), 1.05(s, 9H), 0.36(s, 3H), 0.35(s, 3H)

SIMS m/z : 676, 674(M+1)$^+$

Physicochemical properties of Compound 29 are as follows.

$^1$H-NMR(400MHZ, CDCl$_3$)$\delta$(ppm): 9.89(br s, 1H), 9.31(br s, 1H), 8.55(s, 1H), 6.96(d, 1H, J=2.2Hz), 6.90(s, 1H), 5.99(br s, 1H), 4.23(m, 2H), 4.04(s, 3H), 3.99(m, 1H), 3.95(s, 3H), 3.89(dd, 1H, J=9.8, 3.0Hz), 3.64(br d, 1H, J=11.3Hz) J=9.6, 8.4Hz), 3.33(br s, 1H), 3.23(br s, 1H), 1.28(s, 3H)

SIMS m/z : 562, 560 (M+1)$^+$

IR (KBr) $\nu$max (cm$^{-1}$) 3400, 1680, 1611, 1492, 1309

EXAMPLE 23

Synthesis of Compound 30

Compound 1, 200 mg, was dissolved in 12 ml of methanol and 23 mg of sodium borohydride was added to the solution at 0° C. under cooling. After the mixture was stirred at room temperature for 160 minutes, the reaction mixture was poured into 2 N hydrochloric acid and extracted with chloroform. After washing successively with aqueous sodium hydrogencarbonate solution and saturated aqueous sodium chloride solution, the chloroform layer was dried over anhydrous sodium sulfate. After the solvent was distilled off under reduced pressure, the residue was purified by silica gel column chromatography (100 ml, eluted with n-hexane : ethyl acetate=3 : 2) to give 12 mg of Compound 30 (yield, 6.5%).

Physicochemical properties of Compound 30 are as $^1$H-NMR(400MHz, CDCl$_3$)$\delta$(ppm): 9.43(br s, 1H), 7.87(br s, 1H), 6.88(d, 1H, J=2.2Hz), 6.85(s, 1H), 4.90 (d, 1H, J=5.7Hz), 4.55(dd, 1H, J=10.3, 9.3Hz), 4.40(dd, 1H, J=10.8, 5.2Hz), 4.05(m, 1H), 4.05(s, 3H), 3.93(s, 3H), 3.89(s, 3H), 3.81(dd, 1H, J= 10.1, 3.4Hz), 3.71(m, 1H), 3.49(dd, 1H, J=10.1, 9.6Hz), 1.37(d, 1H, J=6.9Hz), 1.01(s, 9H), 0.30 (s, 3H), 0.29(s, 3H)

IR (KBr) $\nu$max (cm$^{-1}$): 3450, 1618, 1486, 1309, 840

EXAMPLE 24

Synthesis of Compound 31 and 32

Compound 1, 16 mg, was dissolved in 2 ml of THF and n-butyl lithium (0.014 ml, 1.6 M n-hexane solution) was added to the solution at −78° C. After the mixture was stirred for an hour, the reaction mixture was poured into saturated aqueous ammonium chloride solution and extracted with chloroform. After washing successively with aqueous sodium hydrogencarbonate solution and saturated aqueous sodium chloride solution, the chloroform layer was dried over anhydrous sodium sulfate. After the solvent was distilled off under reduced pressure, the residue was purified by preparative thin layer chromatography (developed with n-hexane : ethyl acetate = 2 : 1) to give 5.5 mg of Compound (yield, 33%).

The obtained Compound 31, 5.0 mg, was dissolved in 1.5 ml of THF and 10 ml of phosphate buffer of pH 4 and 0.1 ml of 0.1 M tetrabutyl ammonium fluoride were added to the solution. The mixture was stirred at room temperature for 50 minutes. The reaction mixture was then treated in a manner similar to Example 14 to give 2.5 mg of Compound 32 (yield, 59%).

Physicochemical properties of Compound 31 are as follows.

$^1$H-NMR(100MHz, CDCl$_3$)δ(ppm): 9.40(br s, 1H), 8.20(s,
1H), 6.95(br s, 1H), 6.90(s, 1H), 5.32(s, 1H),
4.7–3.9(m, 4H), 4.02(s, 3H), 3.95(s, 3H), 3.91(s,
3H), 2.71(m, 2H), 1.65(s, 3H), 1.5–0.9(m, 7H),
1.05(s, 9H), 0.35(s, 6H)

EIMS m/z : 729, 727 (M$^+$)

Physicochemical properties of Compound 32 are as follows.

$^1$H-NMR(400MHz, CDCl$_3$)δ(ppm): 9.56(br s, 1H), 9.50(br
s, 1H), 8.50(s, 1H), 7.02(d, 1H, J=4.7Hz), 6.88
(s, 1H), 5.58(s, 1H), 4.63(dd, 1H, J=10.8, 9.3Hz),
4.56(dd, 1H, J=10.8, 4.2Hz), 4.17(s, 3H), 4.15(m,
1H), 4.04(dd, 1H, J=9.8, 3.2Hz), 3.97(s, 3H),
3.92(s, 3H), 3.58(dd, 1H, J=9.8, 9.1Hz), 2.81(ddd,
1H, J=18.0, 8.4, 6.2Hz), 2.60(ddd, 1H, J=18.0,
8.4, 6.2Hz), 1.66(s, 3H), 1.6–1.2(m, 4H), 0.88(t,
3H, J=7.1Hz)

SIMS m/z : 616, 614 (M+1)$^+$

IR (KBr) νmax (cm$^{-1}$): 3400, 1720, 1690, 1610, 1499, 1308

EXAMPLE 25

Synthesis of Compound 33

Compound 33 was obtained in 37.5 mg (yield: 90%) from DC-89B1 in a manner similar to Example 11 except that 37 mg of DC-89B1 was used in place of DC-89B2.

Physicochemical properties of Compound 33 are as follows.

$^1$H-NMR (400MHz, CDCl$_3$)δ(ppm); 9.09 (br s, 1H), 7.46 (s,
1H), 6.78 (s, 1H), 6.60 (d, 1H, J=2.3Hz), 5.46(s, 1H),
4.55 (m, 1H), 4.48 (dd, 1H, J=12.8, 6.4Hz), 4.32 (dd, 1H,
J=12.8, 2.6Hz), 4.08 (s, 3H), 3.93 (s, 3H), 3.88 (s, 3H),
3.88 (dd, 1H, J=19.4, 6.0Hz), 3.79 (s, 3H), 3.71 (dd, 1H,
J=19.4, 5.3Hz), 3.07 (s, 3H), 3.00 (s, 3H), 1.68 (s, 3H)

SIMS m/z 661, 659 (M+1)$^+$

IR (KBr) νmax(cm$^{-1}$): 1715, 1623, 1506, 1388, 1312, 1245, 1161

REFERENCE EXAMPLE 1

*Streptomyces lidicus* DO-89 (FERM BP-988) was used as a seed strain. The strain was inoculated on 200 ml of a seed medium [25 g/l of soluble starch, 5 g/l of glucose, 1 g/l of yeast extract, 10 g/l of Peptone-A (manufactured by Kyokuto Pharmaceutical Co., Ltd.) and 1 g/l of calcium carbonate; pH 7.2 prior to sterilization]in an Erlenmeyer flask of a 2 liter volume followed by shaking culture at 28° C. for 48 hours (200 rpm).

The thus obtained seed culture solution was transferred to 15 liters of a medium having the same composition as described above in a jar fermenter of 30 liter volume in a ratio of 5% (byvolume). Then, shaking culture was performed at 28° C. for 24 hours (rotary number of 200 r.p.m., aerial amount, 15liters/min). The thus obtained culture solution was transferred to 150 liters of a medium having the following composition in a tank jar fermenter of 200 liter volume in a ratio of 10% (by volume). Then, shaking culture was performed at 28° C. (rotary number of 200 r.p.m., aerial amount, 15 liters/min).

Composition of fermentation medium: 50 g/l of maltose, 15 g/lof dry yeast, 25 g/lof EBIOS (productof Asahi Breweries, Ltd.), 10 g/l of KCl, 0.5 g/l of KH$_2$PO$_4$, 0.5 g/l of MgSO$_4$.7H$_2$O, 5 g/l of calcium carbonate (pH 5.0 prior to sterilization; adjusted with 6N H$_2$SO$_4$).

Culturing was conducted for 100 hours without controlling the pH of the medium during the culture. The cells and the precipitates were separated from the culture by filtration to give 100 liters of the filtrate. Separately, 50 liters of n-propanol was added to the cells and the precipitates. After thoroughly mixing, the mixture was filtered to give 45 liters of n-propanol extract. The culture filtrate and the n-propanol extract were combined (140 liters in total). The mixture was passed through 5 liters of DIAION HP-20 (product of Mitsubishi Kasei Corporation) to adsorb the active substance thereto. After washing with water and then with 70% aqueous methanol solution in order, the system was eluted with methanol. The methanol eluate was concentrated and extracted with 10 liters of ethyl acetate. The ethyl acetate extract was concentrated, and n-hexane was added to the concentrate to give crude powders of DC-89A2. The crude powders of DC-89A2 were recrystallized from methanol to give 1 g of pure DC-89A2.

REFERENCE EXAMPLE 2

Culturing was carried out in a manner similar to Reference Example 1 except that the fermentation medium was changed to a medium as described below.

Composition of fermentation medium: 50 g/l of maltose, 15 g/l of dry yeast, 25 g/l of EBIOS (product of Asahi Breweries, Ltd.), 10 g/l of KBr, 0.5 g/l of KH$_2$PO$_4$, 0.5 g/l of MgSO$_4$.7H$_2$O, 5 g/l of calcium carbonate (pH 5.0 prior to sterilization; adjusted with 6N H$_2$SO$_4$).

After a pH of the resulting culture was adjusted to 4.5 with 12N HCl, the cells and the precipitates were separated by filtration to give 100 liters of the filtrate. Separately, 50 liters of n-propanol was added to the cells and the precipitates. After thoroughly mixing, the mixture was filtered to give 45 liters of n-propanol extract. The culture filtrate and the n-propanol extract were combined (140 liters in total). The mixture was passed through 5 liters of DIAION HP-20 to adsorb the active substance thereto. After washing with water and then with 70% aqueous methanol solution in order, the system was eluted with methanol to give the methanol eluate containing DC-89B1 and the methanol eluate containing DC-89B2. The methanol eluate containing DC-89B1 was concentrated and the concentrate was passed through 200 ml of DIAION HP-20SS (product of Mitsubishi Kasei Corporation) followed by eluting with 80% aqueous methanol solution of pH 4.0. The eluate containing DC-89B1 was concentrated and then extracted with ethyl acetate. The ethyl acetate extract was concentrated, and n-hexane was added to the concentrate to give 0.5 g of pure DC-89B1.

The methanol eluate containing DC-89B2 was concentrated and the concentrate was then passed through 500 ml of DIAION HP-20SS followed by eluting with 85% aqueous methanol solution of pH 4.0. The eluate containing DC-89B2 was concentrated and the concentrate was then extracted with ethyl acetate. The ethyl acetate extract was concentrated, and n-hexane was added to the concentrate to give crude powders of DC-89B2. The crude powders of DC-89B2 were recrystallized from methanol to give 1.5 g of pure DC-89B2.

PHARMACEUTICAL PREPARATION 1
(injection)

Compound 13 (10 mg) was dissolved in 50 ml of ethanol, and after stirring, ethanol was removed under reduced pressure. The residue thus obtained was dissolved in 1 l of sterile physiological saline solution. The solution was filtered through a membrane filter with pore size of 0.22 μ (Millipore Inc. FGLD 14200) under a nitrogen gas pressure of 0.5 kg/cm². The filtrate was poured in 20 ml ampules (10 ml in each), and each ampule was sealed in a conventional manner to prepare injections.

What is claimed is:

1. A DC88-A derivative represented by the general formula:

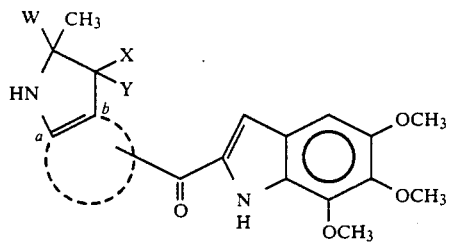

wherein one of X and Y is hydrogen, and the other is $OR^2$ wherein $R^2$ represents hydrogen, $CH_3$, —$COCH_3$ or —COPh wherein Ph represents substituted or unsubstituted phenyl, or X and Y are combined together to form =O;

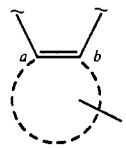

represents

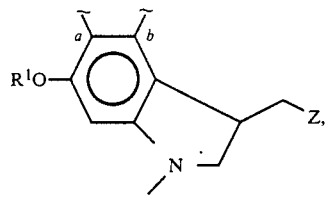

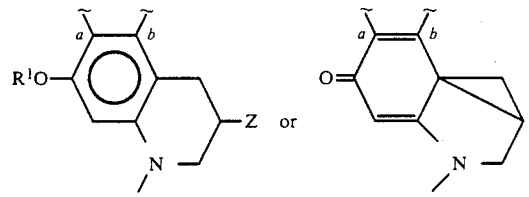

wherein Z represents chlorine or bromine;

$R^1$ represents hydrogen, straight or branched alkyl having 1 to 4 carbon atoms, $COR^3$, $CONR^4R^5$, —$CO_2R^6$, —$SiR^7R^8R^9$ or —$CH_2OCH_3$, wherein $R^3$ represents straight or branched alkyl having 1 to 14 carbon atoms, or unsubstituted or substituted phenyl, each of $R^4$ and $R^5$ independently represents straight or branched alkyl having 1 to 4 carbon atoms, $R^6$ represents straight or branched alkyl having 1 to 4 carbon atoms, allyl or aralkyl each of $R^7$, $R^8$, and $R^9$ independently represents straight or branched alkyl having 1 to 4 carbon atoms;

W represents hydrogen, allyl, —$CO_2R^{10}$, —$COR^4$, or $CH_2OR^2$ wherein $R^{10}$ represents straight or branched alkyl having 1 to 5 carbon atoms, substituted alkyl having 1 to 5 carbon atoms, allyl or benzyl, $R^4$ and $R^2$ have the same significance as defined above; provided that when

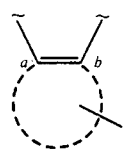

represents

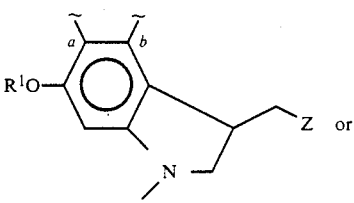

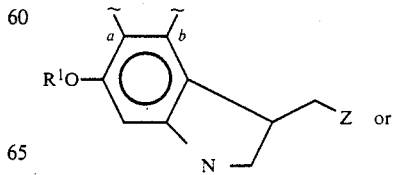

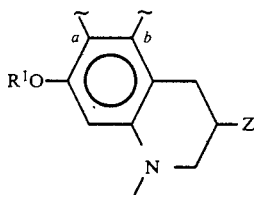

wherein $R^1$ is hydrogen and W is —$CO_2CH_3$ one of X and Y represents hydrogen, and the other represents —$OR^2$ wherein $R^2$ has the same significance as defined above; and that when

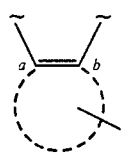

represents

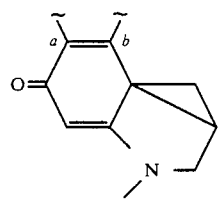

and W is —$CO_2CH_3$, one of X and Y represents hydrogen, and the other represents —$OR^2$ wherein $OR^2$ has the same significance as defined above.

2. A compound according to claim 1, wherein

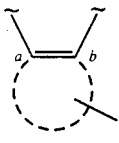

represents

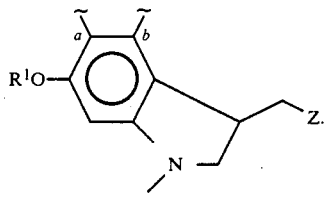

3. A compound according to claim 2, wherein W is selected from the group consisting of —$CO_2CH_3$, —$CO_2C_2H_5$, —$CO_2CH_2CH=CH_2$, —$CO_2CH_2C_6H_5$, —$CO_2CH_2CH_2OH$, —$CH_2CH=CH_2$, —$CH_2OH$, —$CH_2OCOCH_3$, hydrogen and —$CO(CH_2)_3CH_3$; one of X and Y represents hydrogen and the other represents hydroxy, —$OCOCH_3$ or —$OCH_3$; Z is bromine; and $R^1$ is selected from the group consisting of —$Si(CH_3)_2C(CH_3)_3$, —$CH_2OCH_3$, hydrogen, —$COCH_3$, —$CH_3$, —$CON(CH_3)_2$, —$CO_2CH_2CH=CH_2$ and —$CO(CH_2)_{10}CH_3$.

4. A compound according to claim 3, wherein W is —$CO_2CH_3$; one of X and Y represents hydrogen and the other represents hydroxy; and $R^1$ is selected from the group consisting of hydrogen, —$Si(CH_3)_2C(CH_3)_3$, —$COCH_3$, —$CON(CH_3)_2$, —$CO_2CH_2CH=CH_2$ and —$CO(CH_2)_{10}CH_3$.

5. A compound according to claim 4, wherein one of X and Y is hydrogen and the other is hydroxy; and $R^1$ is hydrogen.

6. A compound according to claim 2, wherein W is —$CO_2CH_3$; X and Y are combined together to form=O; Z is bromine; and $R^1$ is —$Si(CH_3)_2C(CH_3)_3$.

7. A compound according to claim 2, wherein W is —$CO_2CH_3$; X and Y are combined together to form=O; Z is bromine; and $R^1$ is —$COCH_3$.

8. A compound according to claim 2, wherein W is —$CO_2CH_3$; X and Y are combined together to form=O; Z is bromine; and $R^1$ is —$CON(CH_3)_2$.

9. A compound according to claim 2, wherein W is —$CO_2CH_3$; X and Y are combined together to form=O; Z is bromine; and $R^1$ is —$CO_2CH_2CH=CH_2$.

10. A compound according to claim 2, wherein W is —$CO_2CH_3$; X and Y are combined together to form=O; Z is bromine; and $R^1$ is —$CO(CH_2)_{10}CH_3$.

11. A compound according to claim 1, wherein

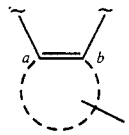

represents

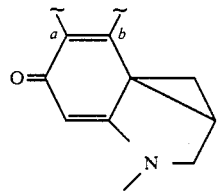

12. A compound according to claim 11, wherein W is —$CO_2CH_2CH=CH_2$; and X and Y are combined together to form=O.

13. A compound according to claim 1, wherein

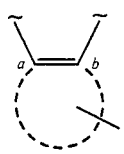

represents

41

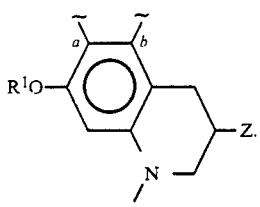

42

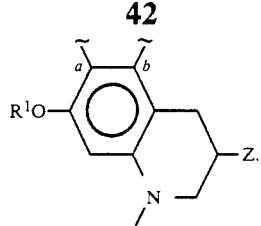

14. A compound according to claim 13, wherein W is —CO₂CH₃; X and Y are combined together to form=O; Z is bromine; and R¹ is —CON(CH₃)₂.

15. A pharmaceutical composition comprising a pharmaceutical carrier and, as an active ingredient, an effective amount of the DC-88A derivatives as defined by claim 1.

* * * * *

14. A compound according to claim 13, wherein W is —CO₂CH₃; X and Y are combined together to form=O; Z is bromine; and R¹ is —CON(CH₃)₂.

15. A pharmaceutical composition comprising a pharmaceutical carrier and, as an active ingredient, an effective amount of the DC-88A derivatives as defined by claim 1.

* * * * *

UNITED STATES PATENT AND TRADEMARK OFFICE
CERTIFICATE OF CORRECTION

PATENT NO. : 5,008,271
DATED : April 16, 1991
INVENTOR(S) : YUTAKA KANDA, ET AL.

It is certified that error appears in the above-identified patent and that said Letters Patent is hereby corrected as shown below:

IN [30] FOREIGN APPLICATION PRIORITY DATA

"64-62572" should read --1-62572--.

COLUMN 2

Line 18, "—CH ," should read -- —$CH_3$,--.
Line 19, "—COCH" should read -- —$COCH_3$--.

COLUMN 5

Line 52, "$^1$represents" should read --$R^{1'}$ represents--.
Line 56, "in" should read --in- --.

COLUMN 6

Line 50, "xethyl" should read --methyl--.
Line 59, "$R^{10'}$ OH" should read --$R^{10'}$OH--.
Line 68, "(Step 2-a)" should read --(Step 2-a).--.

COLUMN 7

Line 27, "$NaA\lambda(OCH_2CO_2OCH_3)_2H_2$" should read
--$NaA\ell(OCH_2CH_2OCH_3)_2H_2$--.

COLUMN 8

Line 26, "$LiA\lambda H_4$" should read --$LiA\ell H_4$--.
Formula (I-2)b, "$CO_2OH$" should read --$CH_2OH$--.

UNITED STATES PATENT AND TRADEMARK OFFICE
CERTIFICATE OF CORRECTION

PATENT NO. : 5,008,271

DATED : April 16, 1991

INVENTOR(S) : YUTAKA KANDA, ET AL.

It is certified that error appears in the above-identified patent and that said Letters Patent is hereby corrected as shown below:

COLUMN 10

Line 30, "$CO_2CH_3$" should read --$CH_2OH$--.

COLUMN 17

Line 56, "𝒵" should read --Z--.

COLUMN 18

Line 7, "z" should read --Z--.
   Line 20, "𝒵" should read --Z--.
   Line 48, "𝒵" should read --Z--.
   Line 50, "H⁰" should read --HO--.

COLUMN 23

Line 11, "once a" should read --once every--.
   Line 64, "J=0.6" should read --J=10.6--.

COLUMN 27

Line 27, "(yield," should read --(yield, 14%).--.

COLUMN 29

Line 39, "AFter" should read --After--.
   Line 64, "3.58(dd, H, J=9.8, 8.9 Hz)," should read
        --3.58(dd, 1H, J=9.8, 8.9 Hz),--.

UNITED STATES PATENT AND TRADEMARK OFFICE
CERTIFICATE OF CORRECTION

PATENT NO. : 5,008,271

DATED : April 16, 1991

INVENTOR(S) : YUTAKA KANDA, ET AL.

It is certified that error appears in the above-identified patent and that said Letters Patent is hereby corrected as shown below:

COLUMN 30

Line 16, "gibe" should read --give--.

COLUMN 32

Line 8, "3 55(dd, 1H, J=10.1, 8.1Hz)," should read --3.55(dd, 1H, J=10.1, 8.1Hz),--.
    Line 15, "and Compound" should read --and Compound 25--.
    Line 22, "followed aqueous" should read --followed by washing with saturated aqueous--.
    Line 48, "1b 7.03(d, 1H, J=2.5Hz)," should read --7.03(d, 1H, J=2.5Hz),--.
    Line 56, "2 42(m, 2H), 1.36(s, 0.9H)," should read --2.42(m, 2H), 1.36(s, 0.9H),--.

COLUMN 33

Line 33, "to" should read --to give 9.2 mg of Compound 27 (yield, 59%).--.
    Line 43, "1.5(s, 3H)" should read --1.51(s, 3H)--.

COLUMN 34

Line 25, "J=11.3Hz)" should read --J=11.3Hz), 3.44 (dd, 1H,--.
    Line 30, "($cm^{-1}$) 3400" should read --($cm^{-1}$):3400--.
    Line 54, "as" should read --as follows:--.

COLUMN 35

Line 17, "Compound (yield, 33%)." should read --Compound 31 (yield, 33%).--.

UNITED STATES PATENT AND TRADEMARK OFFICE
CERTIFICATE OF CORRECTION

PATENT NO. : 5,008,271

DATED : April 16, 1991

INVENTOR(S) : YUTAKA KANDA, ET AL.

It is certified that error appears in the above-identified patent and that said Letters Patent is hereby corrected as shown below:

COLUMN 36

Line 16, "(byvolume)." should read --(by volume).--.
    Line 26, "15 g/lof" should read --15 g/l of--;
             "25 g/lof" should read --25 g/l of--; and
             "(productof" should read --(product of--.

COLUMN 37

Line 34, "1 l" should read --1 $\ell$--.
    Line 42, "DC88-A" should read --DC-88A--.

COLUMN 39

Line 63, "—$CO_2CH_{2CH2}OH$, —$CH_2CH=CH_2$," should read
          -- —$CO_2CH_2CH_2OH$, —$CH_2CH=CH_2$,--.

COLUMN 42

Lines 1-16, Column 42 should be deleted.

Signed and Sealed this

Thirtieth Day of March, 1993

Attest:

STEPHEN G. KUNIN

Attesting Officer      Acting Commissioner of Patents and Trademarks